US010918277B2

(12) United States Patent
Okuda et al.

(10) Patent No.: US 10,918,277 B2
(45) Date of Patent: Feb. 16, 2021

(54) OPHTHALMIC DEVICE

(71) Applicant: TOPCON CORPORATION, Tokyo (JP)

(72) Inventors: Yoki Okuda, Tokyo (JP); Jun Sakai, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 351 days.

(21) Appl. No.: 16/085,642

(22) PCT Filed: Jan. 13, 2017

(86) PCT No.: PCT/JP2017/001113
§ 371 (c)(1),
(2) Date: Sep. 17, 2018

(87) PCT Pub. No.: WO2017/159018
PCT Pub. Date: Sep. 21, 2017

(65) Prior Publication Data
US 2020/0288976 A1 Sep. 17, 2020

(30) Foreign Application Priority Data
Mar. 18, 2016 (JP) .............................. JP2016-055560

(51) Int. Cl.
*A61B 3/15* (2006.01)
*A61B 3/00* (2006.01)
(Continued)

(52) U.S. Cl.
CPC ............ *A61B 3/152* (2013.01); *A61B 3/0075* (2013.01); *A61B 3/102* (2013.01); *A61B 3/1225* (2013.01); *A61B 3/1233* (2013.01)

(58) Field of Classification Search
CPC .. A61B 3/102; A61B 3/14; A61B 3/12; A61B 3/0008; A61B 3/113; A61B 3/13; A61B 3/152
(Continued)

(56) References Cited

U.S. PATENT DOCUMENTS 9,033,503 B2  5/2015  Yoshino et al.
9,706,920 B2  7/2017  Okada et al.
(Continued)

FOREIGN PATENT DOCUMENTS

EP    2 932 888 A1    10/2015
JP    2012196324 A    10/2012
(Continued)

OTHER PUBLICATIONS

International Preliminary Report on Patentability and Written Opinion dated Feb. 14, 2017 in International Application No. PCT/JP2017/001113.
(Continued)

*Primary Examiner* — Hung X Dang
(74) *Attorney, Agent, or Firm* — Xsensus LLP

(57) ABSTRACT

The present invention provides an ophthalmic device capable of minimizing the generation of flare at a lower cost and in a shorter time than in the prior arts when photographing in a state where an optical axis of an examination optical system is deviated from a reference position of a subject eye. The ophthalmic device according to an embodiment of the present invention includes a photographing unit that images a region to be observed of the subject eye through the examination optical system, a first alignment unit that performs alignment on the examination optical system with respect to the subject eye in the optical axis direction and the direction perpendicular to the optical axis direction, an optical system movement unit that moves the examination
(Continued)

optical system from a first position aligned by the first alignment unit to a second position which is deviated from the first position at least in the perpendicular direction, and a second alignment unit that determines an alignment position in the optical axis direction of the examination optical system with respect to the subject eye at the second position based on the positional difference between the first position and the second position and moves the examination optical system to the alignment position along the optical axis direction.

5 Claims, 12 Drawing Sheets

(51) Int. Cl.
*A61B 3/10* (2006.01)
*A61B 3/12* (2006.01)

(58) Field of Classification Search
USPC ........ 351/208, 206, 246, 205, 221, 209, 210
See application file for complete search history.

(56) References Cited

U.S. PATENT DOCUMENTS

| | | | |
|---|---|---|---|
| 9,980,643 B2 | 5/2018 | Fujimura et al. | |
| 2003/0086060 A1 | 5/2003 | Beverly | |
| 2004/0183997 A1 | 9/2004 | Suzuki | |
| 2015/0272432 A1 | 10/2015 | Satake et al. | |
| 2015/0335234 A1* | 11/2015 | Okada | A61B 3/0083 351/208 |

FOREIGN PATENT DOCUMENTS

| | | |
|---|---|---|
| JP | 2013208158 A | 10/2013 |
| JP | 2013244363 A | 12/2013 |
| JP | 2013248376 A | 12/2013 |
| JP | 2014113385 A | 6/2014 |
| JP | 2015150074 A | 8/2015 |

OTHER PUBLICATIONS

English Translation of International Search Report and Written Opinion for International Application No. PCT/JP2017/001113, dated Feb. 14, 2017.

Extended Search Report issued in European Application 17766026.3-1124 dated Feb. 28, 2019.

International Preliminary Report on Patentability and Written Opinion dated Feb. 14, 2018 in International Application No. PCT/JP2017/001113.

* cited by examiner (A)

(B)

(C)

(A)

(B)

(C)

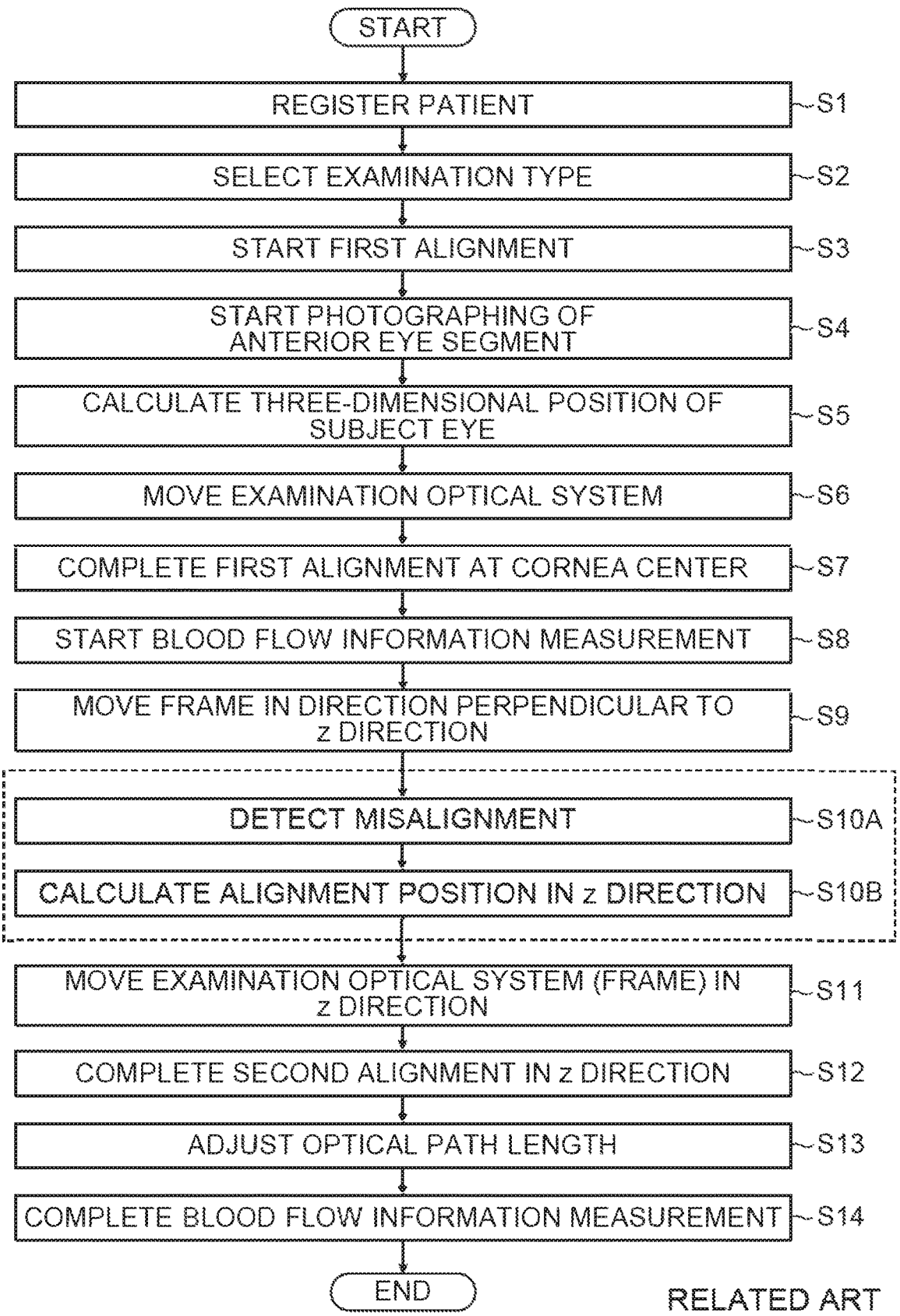

OPHTHALMIC DEVICE

TECHNICAL FIELD

The present invention relates to an ophthalmic device that optically examines a subject eye.

BACKGROUND ART

As an ophthalmic device that optically examines a subject eye, for example, an optical interference tomograph meter or the like that acquires a tomographic image using optical coherence tomography (OCT) is well known.

When an examination is performed using such an ophthalmic device, positioning between an examination optical system (apparatus-side optical system) and the subject eye is extremely important from the standpoint of accuracy and exactitude of an examination. This positioning is called "alignment." The alignment includes an operation of matching the optical axis of an examination optical system with a reference position (e.g., corneal center) of the subject eye (xy alignment) and an operation of adjusting a distance between the subject eye and the examination optical system (z alignment).

For example, PTL 1 describes an ophthalmic device that photographs an anterior eye segment of the subject eye from different directions using two or more photographing units, analyzes two or more images acquired through the photographing, and adjusts alignment of the examination optical system with respect to the subject eye based on the calculation result of the three-dimensional position of the subject eye.

The ophthalmic device that obtains a tomographic image using OCT is also used to measure blood flow information of the blood flowing through the blood vessels of the eye fundus of the subject eye. In this blood flow information measurement, since the velocity of the fundus oculi blood flow is calculated using a technique of Doppler shift OCT, when the angle formed by the incident direction of signal light on the subject eye and the direction in which the blood vessel of the eye fundus extends is 90°, the blood flow velocity cannot be calculated (see PTL 2). Therefore, when blood flow information is measured, it is necessary to image a tomographic image of the eye fundus with the optical axis of the examination optical system deviated from a reference position of the subject eye.

When photographing is performed with the optical axis of the examination optical system deviated from the reference position of the subject eye in this way, it is known that flare (noise light) is more likely to occur (see PTL 3). For this reason, the ophthalmic device according to PTL 3 detects an amount of misalignment of the examination optical system with respect to the subject eye in the xy direction (up-down and left-right directions) based on a taken image of the anterior eye segment of the subject eye, calculates an alignment position in the z direction (front-back direction) of the examination optical system based on the detection result and performs alignment in the z direction. Flare generation can thereby be suppressed.

CITATION LIST

Patent Literature

{PTL 1} Japanese Patent Application Laid-Open No. 2013-248376

{PTL 2} Japanese Patent Application Laid-Open No. 2013-208158

{PTL 3} Japanese Patent Application Laid-Open No. 2012-196324

SUMMARY OF INVENTION

Technical Problem

When blood flow information is measured using OCT by the ophthalmic device described in PTL 3, it is necessary to detect an amount of misalignment in the xy direction of the examination optical system with respect to the subject eye from the taken image of the subject eye and calculate an alignment position in the z direction of the examination optical system based on the detection result of this amount of misalignment. For this reason, the ophthalmic device described in PTL 3 requires time to determine the alignment position in the z direction in which it is possible to suppress flare generation. Note that the time required for the determination can be shortened using a high performance computation processing apparatus, but in this case, there is a problem that the manufacturing cost of the ophthalmic device increases.

The present invention has been implemented in view of the above circumstances and aims to provide an ophthalmic device capable of suppressing flare generation at a lower cost and in a shorter time than in prior arts, when photographing is performed in a state where the optical axis of an examination optical system is deviated from a reference position of a subject eye.

Solution to Problem

An ophthalmic device to achieve an object of the present invention includes: a photographing unit configured to photograph a region to be observed of a subject eye through an examination optical system; a first alignment unit configured to perform alignment of the examination optical system with respect to the subject eye in an optical axis direction and alignment in a perpendicular direction to the optical axis direction; an optical system movement unit configured to move the examination optical system from a first position aligned by the first alignment unit to a second position deviated at least in the perpendicular direction; and a second alignment unit configured to determine an alignment position in the optical axis direction of the examination optical system at the second position with respect to the subject eye based on a positional difference between the first position and the second position, and move the examination optical system to the alignment position along the optical axis direction.

According to this ophthalmic device, it is possible to determine the alignment position in the optical axis direction of the examination optical system at the second position with respect to the subject eye based on a positional difference between the first position and the second position, and thereby determine the alignment position more simply and more quickly than in the prior arts.

In the ophthalmic device according to another aspect of the present invention, the examination optical system includes: an interference optical system configured to divide light emitted from a light source into signal light and reference light, irradiate the region to be observed with the signal light and guide interference light between the signal light reflected by the region to be observed and the reference light to the photographing unit; an optical path length changing unit provided in the interference optical system and configured to change an optical path length of at least one of the signal light and the reference light; and an adjustment control unit configured to control the optical path length changing unit to adjust the optical path length according to a distance and a direction that the examination optical system moves in the optical axis direction in alignment by the second alignment unit. Thereby, even when alignment by the second alignment unit is performed, it is possible to maintain the constant optical path length difference between the signal light and the reference light before and after the alignment.

An ophthalmic device according to a further aspect of the present invention, further includes: a base; and a frame movably supported with respect to the base at least in the perpendicular direction, in which the examination optical system and the photographing unit are disposed on the frame and the optical system movement unit moves the frame to move the examination optical system from the first position to the second position. It is possible to move the examination optical system from the first position to the second position by only moving the frame. In addition, it is possible to determine the alignment position based on the moving direction and the amount of movement of the frame.

An ophthalmic device according to a further aspect of the present invention, further includes: a storage unit configured to store a correspondence relation between the positional difference and the alignment position, in which the second alignment unit refers to the correspondence relation stored in the storage unit based on the positional difference and determines the alignment position. This allows the alignment position to be determined more simply and more quickly than in the prior arts.

An ophthalmic device according to a still further aspect of the present invention, further includes: a subject eye position acquisition unit configured to acquire a three-dimensional position of the subject eye; and a positional deviation information acquisition unit configured to acquire positional deviation information of the examination optical system in the optical axis direction and the perpendicular direction with respect to the subject eye based on the three-dimensional position acquired by the subject eye position acquisition unit, in which the first alignment unit performs alignment of the examination optical system through automatic control or manual control based on the positional deviation information acquired by the positional deviation information acquisition unit. This makes it possible to align the examination optical system with respect to a reference position it the subject eye.

Advantageous Effects of Invention

The ophthalmic device of the present invention can prevent flare generation at lower cost and in a shorter time than in the prior arts when photographing is performed in a state where the optical axis of the examination optical system is deviated from a reference position of the subject eye.

BRIEF DESCRIPTION OF DRAWINGS

FIG. 12 is a flowchart illustrating a flow of measurement processing of blood flow information of the eye fundus in a comparative example.

DESCRIPTION OF EMBODIMENTS

An embodiment of an ophthalmic device according to the present invention will be described in detail with reference to the accompanying drawings. The ophthalmic device according to the present invention is used for an optical examination of a subject eye. An optical interference tomograph meter is taken as an example to describe such an ophthalmic device in the present embodiment.

In the present specification, an image (tomographic image) acquired by OCT may be generically referred to as an "OCT image." A measurement operation for forming an OCT image may be referred to as an "OCT measurement." Note that contents of the literatures described in the present specification may be referred to in the contents of the following embodiment as appropriate.

In the following embodiment, an optical interference tomograph meter using spectral domain type OCT provided with a low coherence light source and a spectroscope will be described, but the present invention is also applicable to optical interference tomograph meters of other types, for example, a swept source type or en-face type OCT. Note that the swept source type OCT is a technique that scans (wavelength sweeping) a wavelength of light radiated onto an object to be measured, detects interference light obtained by overlapping reflected light of light of each wavelength and reference light, acquires a spectral intensity distribution, applies Fourier transform to the spectral intensity distribution and thereby images the form of the object to be measured. On the other hand, the en-face OCT irradiates an object to be measured with light having a predetermined beam diameter, analyzes an interference light component obtained by overlapping the reflected light and the reference light, to thereby form an image of the object to be measured on a section orthogonal to the light traveling direction. The swept source type OCT is also called a "full-field type."

Although an apparatus which combines an OCT apparatus and a fundus camera will be described in the following embodiment, the apparatus to which the present invention is applied is not limited to such a composite apparatus. The present invention is also applicable to an ophthalmic device as a single unit.

<Overall Configuration of Ophthalmic Device>

Figure 1:
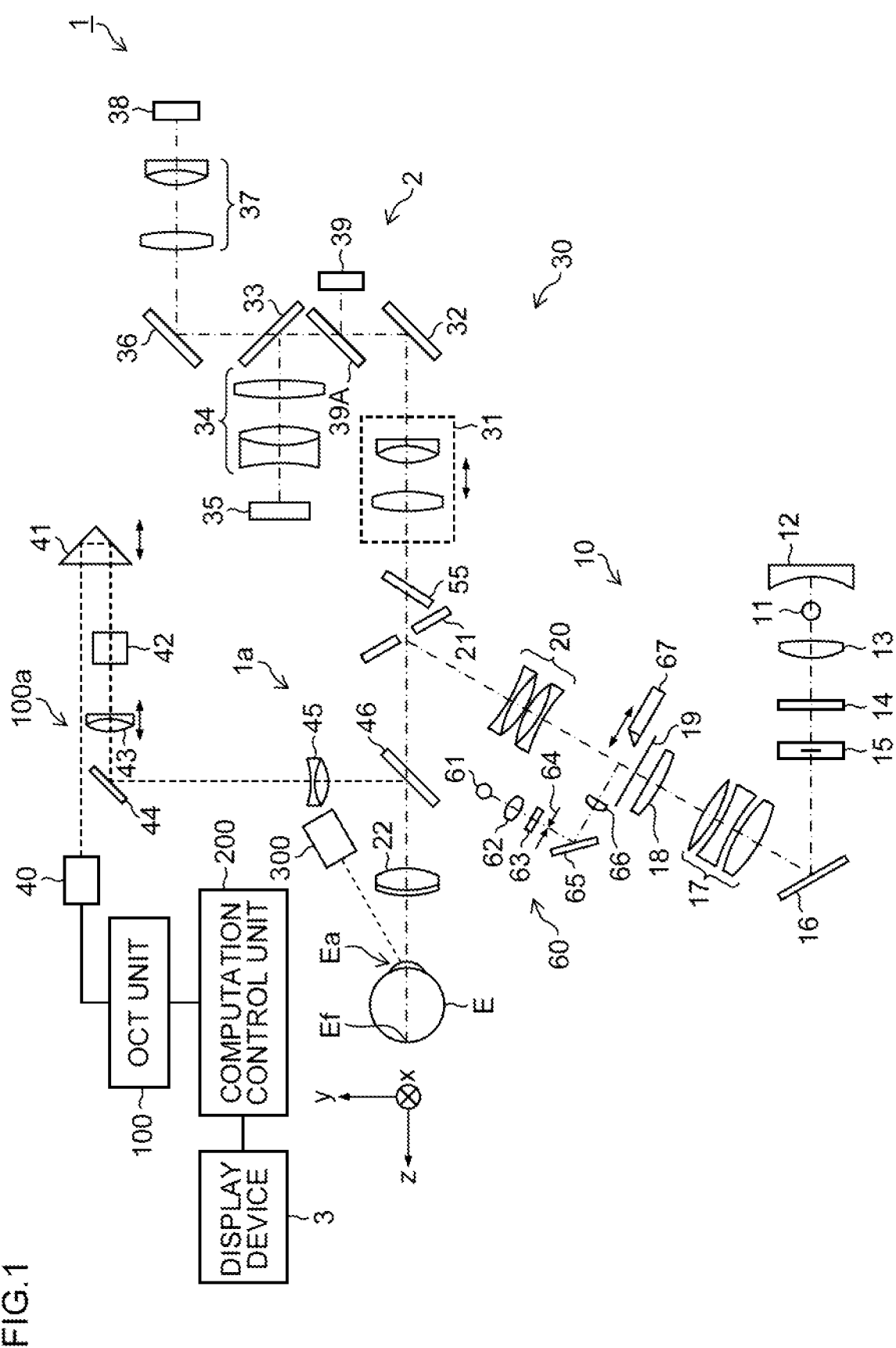
FIG. 1 is a schematic diagram illustrating an example of a configuration of an ophthalmic device.

FIG. 1 is a schematic diagram illustrating an example of a configuration of an ophthalmic device 1. As shown in FIG. 1, the ophthalmic device 1 is provided with a fundus camera unit 2, a display device 3, an OCT unit 100 and a computation control unit 200. The fundus camera unit 2 has an optical system almost identical to a conventional fundus camera. The OCT unit 100 is provided with an interference optical system 100a (see FIG. 2) for acquiring an OCT image of an eye fundus Ef (corresponding to a region to be observed of the present invention) of a subject eye E. A photographing optical system 30 of the fundus camera unit 2 and the interference optical system 100a of the OCT unit 100 constitute an examination optical system 1a of the present invention. The computation control unit 200 is provided with a computer that executes various computation processes and control processes or the like.

<Fundus Camera Unit>

The fundus camera unit 2 is provided with an optical system to acquire a two-dimensional image (fundus image) expressing a surface form of the eye fundus Ef. Examples of the fundus image include an observation image and a photographed image. The observation image is, for example, a monochrome moving image formed at a predetermined frame rate using near-infrared light. Note that when the optical system is focused on the anterior eye segment Ea of the subject eye E, the fundus camera unit 2 can acquire an observation image of the anterior eye segment Ea. The photographed image may be, for example, a color image obtained through flash emission of visible light or a monochrome still image obtained by using near-infrared light or visible light as illumination light. The fundus camera unit 2 may be configured to be able to acquire other images such as a fluorescein fluorescent image, an indocyanine green fluorescent image or an autofluorescent image.

The fundus camera unit 2 is provided with an illumination optical system 10 and a photographing optical system 30. The illumination optical system 10 irradiates the eye fundus Ef with illumination light. The photographing optical system 30 guides the fundus reflection light (light reflected from the fundus) of this illumination light to CCD (charge coupled device) type or CMOS (complementary metal oxide semiconductor) type image sensors 35 and 38. The photographing optical system 30 also guides the signal light from the OCT unit 100 to the eye fundus Ef and also guides the signal light through the eye fundus Ef, to the OCT unit 100.

An observation light source 11 of the illumination optical system 10 is made up of a halogen lamp, for example. Light (observation illumination light) outputted from the observation light source 11 is reflected by a reflector 12 having a curved reflection surface, passes through a condensing lens 13, transmits a visible light cut filter 14 and thereby becomes near-infrared light. Furthermore, the observation illumination light once converges in the vicinity of a photographing light source 15, is reflected by a mirror 16, and passes through relay lenses 17 and 18, a diaphragm 19 and a relay lens 20. The observation illumination light is then reflected by a peripheral portion (region around an aperture) of a perforated mirror 21, passes through a dichroic mirror 46, is then refracted by an objective lens 22 and illuminates the eye fundus Ef. Note that an LED (light emitting diode) may also be used as the observation light source.

The fundus reflection light of the observation illumination light is refracted by the objective lens 22, passes through the dichroic mirror 46, the hole formed in the central region of the perforated mirror 21 and a dichroic mirror 55, passes through a focusing lens 31 and is reflected by a mirror 32. The fundus reflection light further passes through a half mirror 39A, is reflected by a dichroic mirror 33, is condensed by a condensing lens 34 to form all image of the fundus reflection light on a light receiving surface of the image sensor 35. The image sensor 35 detects the fundus reflection light at a predetermined frame rate, for example. The display device 3 displays an image (observation image) based on the fundus reflection light detected by the image sensor 35. Note that when the photographing optical system is focused on the anterior eye segment Ea, the display device 3 displays an observation image of the anterior eye segment Ea.

The photographing light source 15 is made up of a xenon lamp, for example. Light (photographing illumination light) outputted from the photographing light source 15 passes through a path similar to that of the observation illumination light and is radiated onto the eye fundus Ef. Furthermore, the fundus reflection light of the photographing illumination light is guided to the dichroic mirror 33 after passing through a path similar to that of the observation illumination light, passes through the dichroic mirror 33, is reflected by a mirror 36, and is condensed by a condensing lens 37 to form an image on a light receiving surface of the image sensor 38. The display device 3 displays the image (photographed image) based on the fundus reflection light detected by the image sensor 38. Note that the display device 3 that displays the observation image may be the same as, or different from the display device 3 that displays the photographed image. When similar photographing is performed by illuminating the subject eye E with infrared light, a photographed image of infrared light is displayed. Furthermore, an LED can also be used as a photographing light source.

An LCD (liquid crystal display) 39 displays a fixation visual target or a visual target for visual acuity measurement. The fixation visual target is an index for making the subject eye E fixed and used when fundus photography or OCT measurement.

A part of the light outputted from the LCD 39 is sequentially reflected through the half mirror 39A and the mirror 32, sequentially passes through the focusing lens 31, the dichroic mirror 55, the hole of the perforated mirror 21 and the dichroic mirror 46, then is refracted by the objective lens 22 and projected onto the eye fundus Ef.

By changing the display position of the fixation visual target on a screen of the LCD 39, it is possible to change the projection direction of the fixation visual target for the subject eye E, that is, a fixation eye position of the subject eye E. Examples of the fixation eye position of the subject eye E include, as with the conventional fundus camera, for example, a position for acquiring an image centered on the macular part of the eye fundus Ef, a position for acquiring an image centered on the optic papilla and a position for acquiring an image centered on the eye fundus between the macular part and the optic papilla. The display position of the fixation visual target can be changed arbitrarily.

Note that means for projecting the fixation visual target onto the subject eye E is not limited to this. For example, an LED group composed of an array of a plurality of LEDs may be provided and the position of the fixation visual target can be changed by selectively turning on these LEDs. The fixation eye position can also be changed by providing one or more movable LEDs.

The fundus camera unit 2 is provided with a focus optical system 60. The focus optical system 60 generates an index (split index) to focus on the eye fundus Ef.

When adjusting focus, a reflection surface of a reflection rod 67 is diagonally placed on an optical path of the illumination optical system 10. Light (focus light) outputted from an LED 61 of the focus optical system 60 passes through a relay lens 62, is separated into two luminous fluxes by a split index plate 63, passes through a double perforated diaphragm 64, is reflected by a mirror 65, is condensed by a condensing lens 66 to once form an image of the light on the reflection surface of the reflection rod 67, and then is reflected by the surface. Furthermore, the focus light passes through the relay lens 20, is reflected by the perforated mirror 21, passes through the dichroic mirror 46, is refracted by the objective lens 22 and is projected onto the eye fundus Ef.

The fundus reflection light of the focus light is detected by the image sensor 35 after passing through a path similar to that of the observation illumination light. An image (split index) received by the image sensor 35 is displayed on the display device 3 together with the observation image. As with the prior arts, the computation control unit 200 analyzes the position of the split index, moves the focusing lens 31 and the focus optical system 60 to automatically adjust the focus (autofocus function). The focus may also be adjusted manually while visually checking the split index.

The dichroic mirror 46 causes the OCT measurement optical path to be branched from the optical path for fundus photography. The dichroic mirror 46 reflects light in the wavelength band used for OCT measurement and transmits light for fundus photography. A collimator lens unit 40, an optical path length changing unit 41, a galvanoscanner 42, a focusing lens 43, a mirror 44 and a relay lens 45 are provided on this optical path for OCT measurement in this order from the OCT unit 100 side. These components constitute part of the aforementioned interference optical system 100a.

The optical path length changing unit 41 is enabled to move in a direction indicated by an arrow shown in FIG. 1 to change the optical path length of the optical path for OCT measurement (signal light LS Which will be described later, see FIG. 2). The change in this optical path length is used to correct the optical path length according to the eye axial length of the subject eye E and adjust the interference status or the like. The optical path length changing unit 41 includes a corner cube and a mechanism for moving the corner cube.

The galvanoscanner 42 changes the traveling direction of light (signal light LS, see FIG. 2) that passes through the optical path for OCT measurement. The galvanoscanner 42 includes, for example, a galvanomirror that performs scanning with the signal light LS in the x direction, a galvanomirror that performs scanning with the signal light LS in the y direction and a mechanism for driving these galvanomirrors independently. This makes it possible to scan the eye fundus Ef with the signal light LS.

Figure 5A:
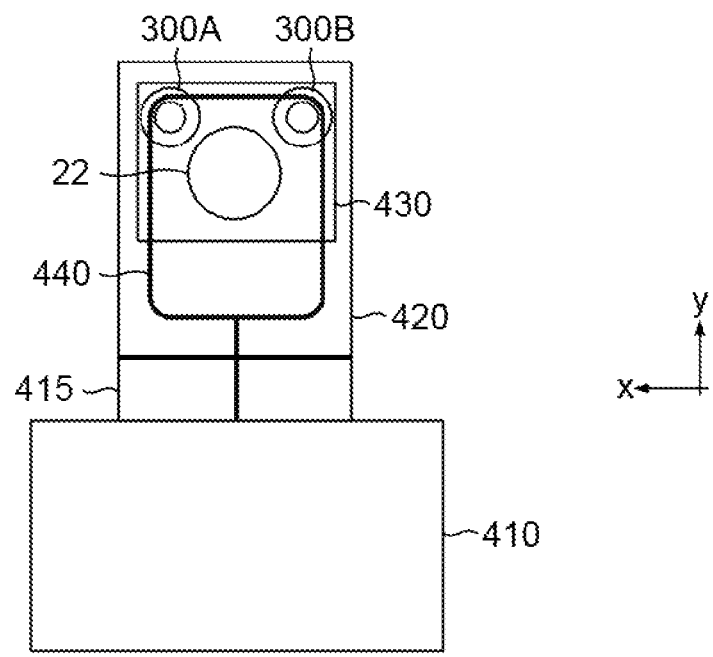
FIG. 5A is a front view of the ophthalmic device.

The fundus camera unit 2 is provided with an anterior eye segment camera 300. The anterior eye segment camera 300 images the anterior eye segment Ea substantially simultaneously from different directions. In the present embodiment, two cameras are provided on the surface of the fundus camera unit 2 on a subject side (see anterior eye segment cameras 300A and 300B shown in FIG. 5A). As shown in FIG. 1 and FIG. 5A, the anterior eye segment camera 300A and the 300B are provided at positions deviated (shifted) from the optical path of the illumination optical system 10 and the optical path of the photographing optical system 30. Hereinafter, the two anterior eye segment cameras 300A and 300B will be collectively designated by reference numeral 300.

Although the two anterior eye segment cameras 300A and 300B are provided in the present embodiment, the number of the anterior eye segment cameras 300 may be an arbitrary determined to be equal to or greater than 2. In the present embodiment, the anterior eye segment camera 300 is provided separately from the illumination optical system 10 and the photographing optical system 30, but similar anterior eye segment photographing can be performed using at least the photographing optical system 30. That is, the anterior eye segment cameras 300 may be configured such that one of the two or more anterior eye segment cameras includes the photographing optical system 30.

Note that "substantially simultaneous" means that, in photographing by the two or more anterior eye segment cameras, the anterior eye segment cameras can tolerate some degree of difference in photographing timing at which eye movement can be neglected. This makes it possible to acquire images when the subject eye E is located at substantially the same position (orientation) by the two or more anterior eye segment cameras 300.

Photographing by the two or more anterior eye segment cameras 300 may be either moving image photographing or still image photographing. In the case of moving image photographing, it is possible to realize substantially simultaneous anterior eye segment photography by controlling photographing start timings of the anterior eye segment cameras 300 to match each other, or controlling the frame rate and photographing timing of each frame to match each other. On the other hand, in the case of still image photographing, it is possible to realize substantially simultaneous anterior eye segment photographing by controlling photographing timings to match each other.

In the present embodiment, positioning (alignment) of the examination optical system 1a with respect to the subject eye E is performed using the two anterior eye segment cameras 300A and 300B.

<OCT Unit>

Figure 2:
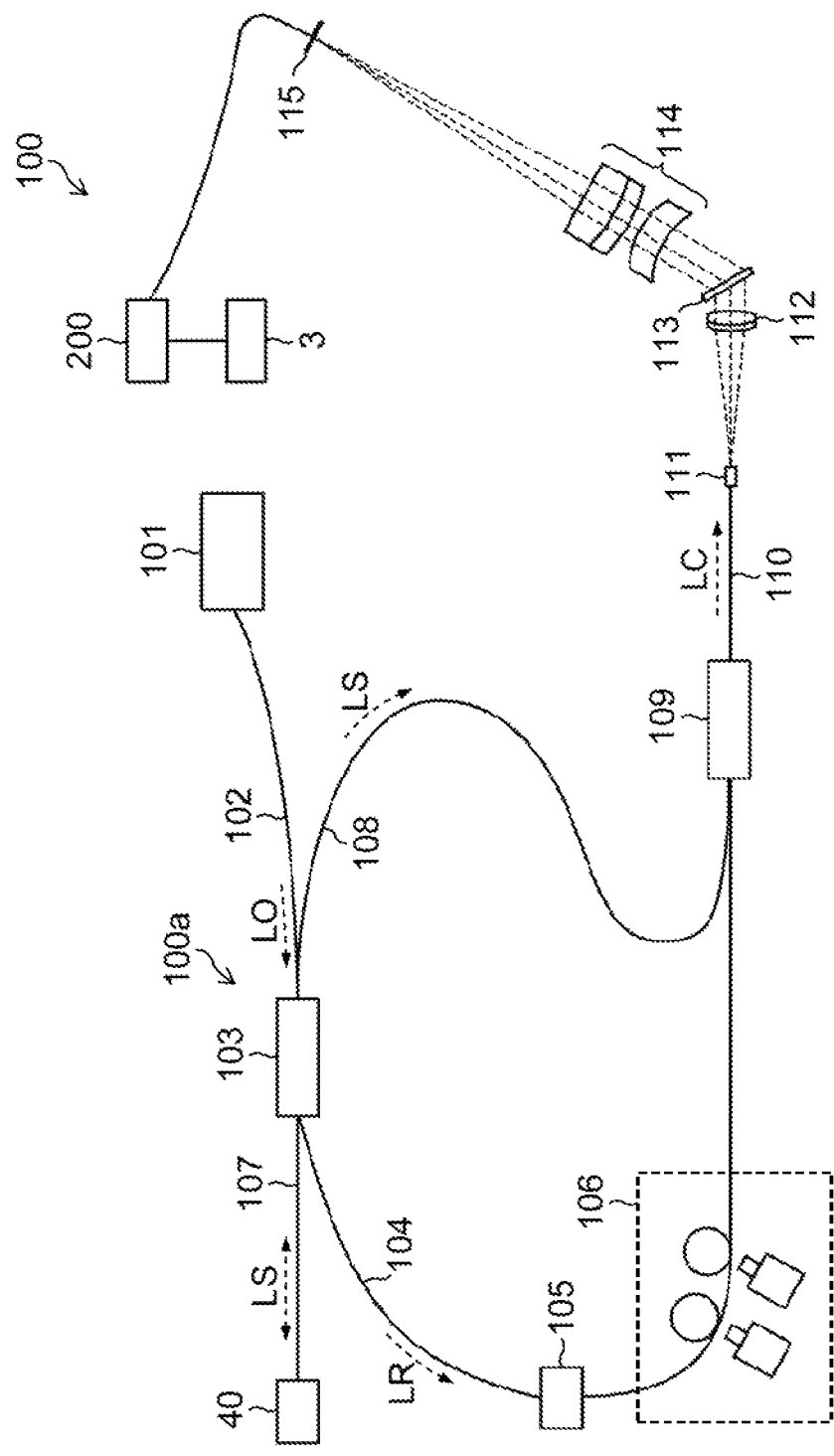
FIG. 2 is a schematic diagram illustrating an example of a configuration of an OCT unit.

FIG. 2 is a schematic diagram illustrating an example of the configuration of the OCT unit 100. As shown in FIG. 2, the OCT unit 100 is provided with the interference optical system 100a to acquire an OCT image of the eye fundus Ef.

The interference optical system 100a has a configuration similar to that of a conventional spectral domain type OCT apparatus. That is, the interference optical system 100a has a configuration to divide low coherence light into reference light LR and signal light (also referred to as "measurement light") LS, cause the signal light LS via the eye fundus Ef and the reference light LR via the reference optical path to interfere with each other to generate interference light LC, and detect the spectral component of the interference light LC.

Note that a well-known technique in accordance with the type of OCT can be arbitrarily applied for the configuration of the OCT unit 100. For example, in the case of a swept source type OCT apparatus, a wavelength sweeping light source is provided instead of a light source that outputs low coherence light, and no optical member is provided for spectrally resolving the interference light.

The light source unit 101 outputs wideband low coherence light LO. The low coherence light LO includes, for example, a wavelength band of a near-infrared region (approximately 800 nm to 900 nm) and has a time coherence length on the order of several tens of micrometers. Note that near-infrared light having a wavelength band not visible to human eyes, for example, a central wavelength of on the order of 1040 to 1060 nm may be used as low coherence light LO.

The light source unit 101 is provided with a light output device such as a super luminescent diode (SLD), an LED and an SOA (semiconductor optical amplifier).

The low coherence light LO outputted from the light source unit 101 is guided to a fiber coupler 103 by an optical fiber 102 and divided into signal light LS and reference light LR.

The reference light LR is guided by an optical fiber 104 to reach a light attenuation device (attenuator) 105. The light attenuation device 105 automatically adjusts the light quantity of the reference light LR guided to the optical fiber 104 under the control of the computation control unit 200. The reference light LR, whose the light quantity is adjusted by the light attenuation device 105, is guided by the optical fiber 104 to reach a polarized wave adjuster (polarized wave controller) 106. The polarized wave adjuster 106, for example, applies stress to the loop-shaped optical fiber 104 from outside, and thereby adjusts a polarization state of the reference light LR which is guided through the optical fiber 104. Note that the configuration of the polarized wave adjuster 106 is not limited to this, but an arbitrary well-known technique can be used. The reference light LR, whose polarization state is adjusted by the polarized wave adjuster 106, reaches a fiber coupler 109.

On the other hand, the signal light LS generated by the fiber coupler 103 is guided by an optical fiber 107 and transformed into parallel luminous flax by the collimator lens unit 40. Furthermore, as shown in FIG. 1 described above, the signal light LS reaches the dichroic mirror 46 via the optical path length changing unit 41, the galvanoscanner 42, the focusing lens 43, the mirror 44 and the relay lens 45. The signal light LS is reflected by the dichroic mirror 46, refracted by the objective lens 22 and radiated onto the eye fundus Ef. The signal light LS is scattered (or reflected) at various depth positions of the eye fundus Ef. Backward scattered light of the signal light LS by the eye fundus Ef travels backward through the same path as that of the outward passage, is guided by the fiber coupler 103 and reaches the fiber coupler 109 via an optical fiber 108.

The fiber coupler 109 causes the backward scattered light of the signal light LS and the reference light LR via the optical fiber 104 to interfere with each other to thereby generate interference light LC. This interference light LC is guided by an optical fiber 110 and emitted from an emitting end 111. Furthermore, the interference light LC is transformed into a parallel luminous flux by a collimator lens 112, spectrally diffracted (spectrally resolved) by a diffraction grating 113, condensed by a condensing lens 114 and projected onto the light receiving surface of a CCD or CMOS type image sensor 115. Note that the diffraction grating 113 shown in FIG. 2 is of a transmission type, but spectral elements of other modes such as reflection type diffraction grating can also be used.

The image sensor 115 corresponds to a photographing unit of the present invention, and, for example, a line sensor is used. For example, a CCD type image sensor 115 detects each spectral component of the spectrally diffracted interference light LC and converts the spectral component to charge. The image sensor 115 accumulates the charge, generates a detection signal and sends the detection signal to the computation control unit 200. An OCT image of the eye fundus Ef is thereby obtained. By moving the aforementioned optical path length changing unit 41 and changing the optical path length difference between the signal light LS and the reference light LR, OCT images in various depths of the eye fundus Ef are obtained.

Note that although a Michelson type interferometer is adopted in the present embodiment, an arbitrary type such as Mach-Zehnder type interferometer can be adopted as appropriate. Furthermore, although the optical path length changing unit 41 changes the optical path length of the signal light LS in the present embodiment, the optical path length of the signal light LS can be changed by moving the optical system itself which contributes to OCT measurement with respect to the subject eye E. Furthermore, the optical path length of the reference optical path may be changed by disposing a reflector (reference mirror) in the reference optical path of the reference light LR and causing the reference mirror to move in the traveling direction of the reference light LR instead of changing the optical path length of the signal light LS. Furthermore, it is also possible to combine a change in the optical path length of the signal light LS and a change in the optical path length of the reference light LR.

<Computation Control Unit>

Returning to FIG. 1, the computation control unit 200 analyzes the detection signal inputted from the image sensor 115, forms an OCT image of the eye fundus Ef and causes the display device 3 to display the OCT image of the eye fundus Ef. Note that the computation processing for forming the OCT image is similar to that of the conventional spectral domain type OCT apparatus.

Furthermore, the computation control unit 200 performs operation control of the respective units of the fundus camera unit 2 and the OCT unit 100.

As control of the fundus camera unit 2, the computation control unit 200 performs operation control of the observation light source 11, operation control of the photographing light source 15, operation control of the LED 61, operation control of the LCD 39, movement control of the focusing lenses 31 and 43, movement control of the reflection rod 67, movement control of the focus optical system 60, movement control of the optical path length changing unit 41, operation control of the galvanoscanner 42, operation control of the anterior eye segment camera 300 or the like.

As control of the OCT unit 100, the computation control unit 200 performs operation control of the light source unit 101, operation control of the light attenuation device 105, operation control of the polarized wave adjuster 106, operation control of the image sensor 115 or the like.

As with, for example, a conventional computer, the computation control unit 200 is provided with a microprocessor, a RAM (random access memory), a ROM (read only memory), a hard disk drive, and a communication interface or the like. The storage apparatus such as a hard disk drive stores computer program and data to control the ophthalmic device 1. The computation control unit 200 may be provided with various circuit substrates such as a circuit substrate for forming an OCT image. Furthermore, the computation control unit 200 may be provided with operation devices (input devices) such as a keyboard and a mouse, and a display device such as an LCD.

The fundus camera unit 2, the display device 3, the OCT unit 100 and the computation control unit 200 may be constructed integrally (that is, in a single casing) or separately in two or more casings.

(Measurement of Blood Flow Information)

The computation control unit 200 (ophthalmic device 1) according to the present embodiment performs blood flow information measurement to generate blood flow information relating to a concerned blood vessel of the eye fundus Ef. Here, the blood flow information is information relating to a blood flow such as information indicating a blood flow velocity and a blood flow rate.

During blood flow information measurement, two kinds of scans (first scan and second scan) are performed on the eye fundus Ef. In the first scan, a first cross section that crosses the concerned blood vessel of the eye fundus Ef is scanned iteratively with the signal light LS. In the second scan, a second cross section that crosses the concerned blood vessel and is located in the vicinity of the first cross section is scanned with the signal light LS. Here, the first cross section and the second cross section are preferably orthogonal to the running direction of the concerned blood vessel.

Figure 3:
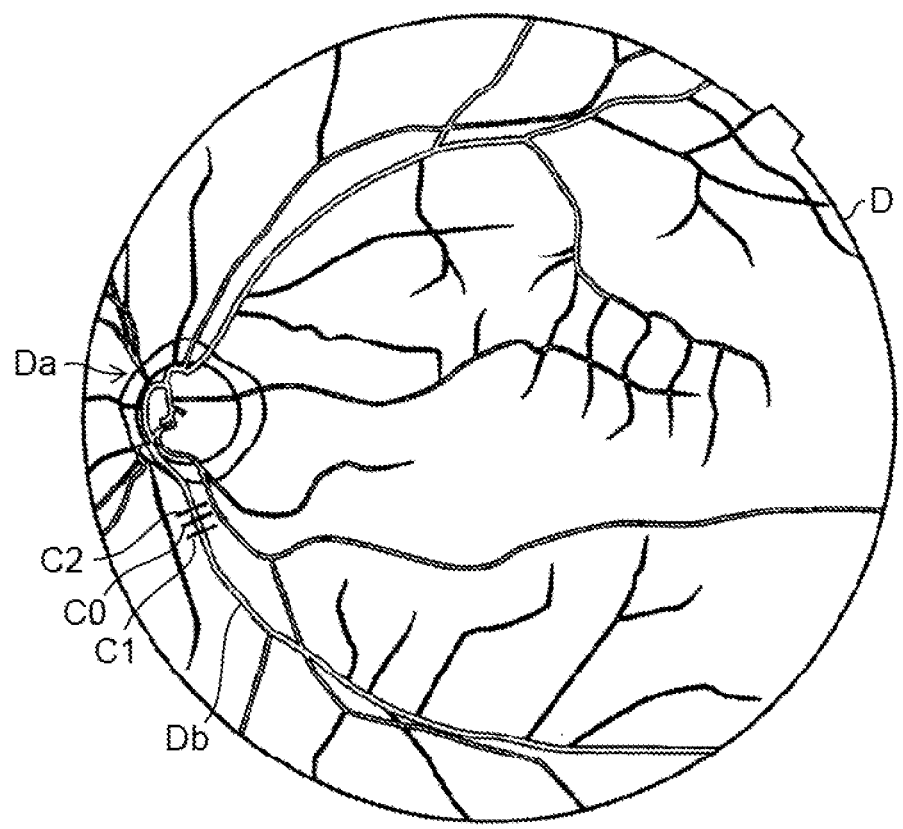
FIG. 3 is an explanatory diagram illustrating an example of a first scan and a second scan when measuring blood flow information.

FIG. 3 is an explanatory diagram for describing an example of the first scan and the second scan during the blood flow information measurement. As shown in an eye fundus image (fundus image) D in FIG. 3, one first cross section C0 and two second cross sections C1 and C2 are set so as to cross a predetermined concerned blood vessel Db in the vicinity of the optic papilla Da of the eye fundus Ef in the present embodiment. Of the two second cross sections C1 and C2, one is located upstream of the concerned blood vessel Db with respect to the first cross section C0 and the other is located downstream thereof.

The first scan is preferably performed for at least 1 cardiac cycle of a patient's heart. Thus, blood flow information for all time phases of the heart is obtained. Note that a time period during which the first scan is executed may be a predetermined time period or a time period set for each patient or each examination. In the former case, a longer time period than a general cardiac cycle is set (e.g., 2 seconds). In the latter case, examination data such as the patient's cardiogram is referenced.

<Control System>

Figure 4:
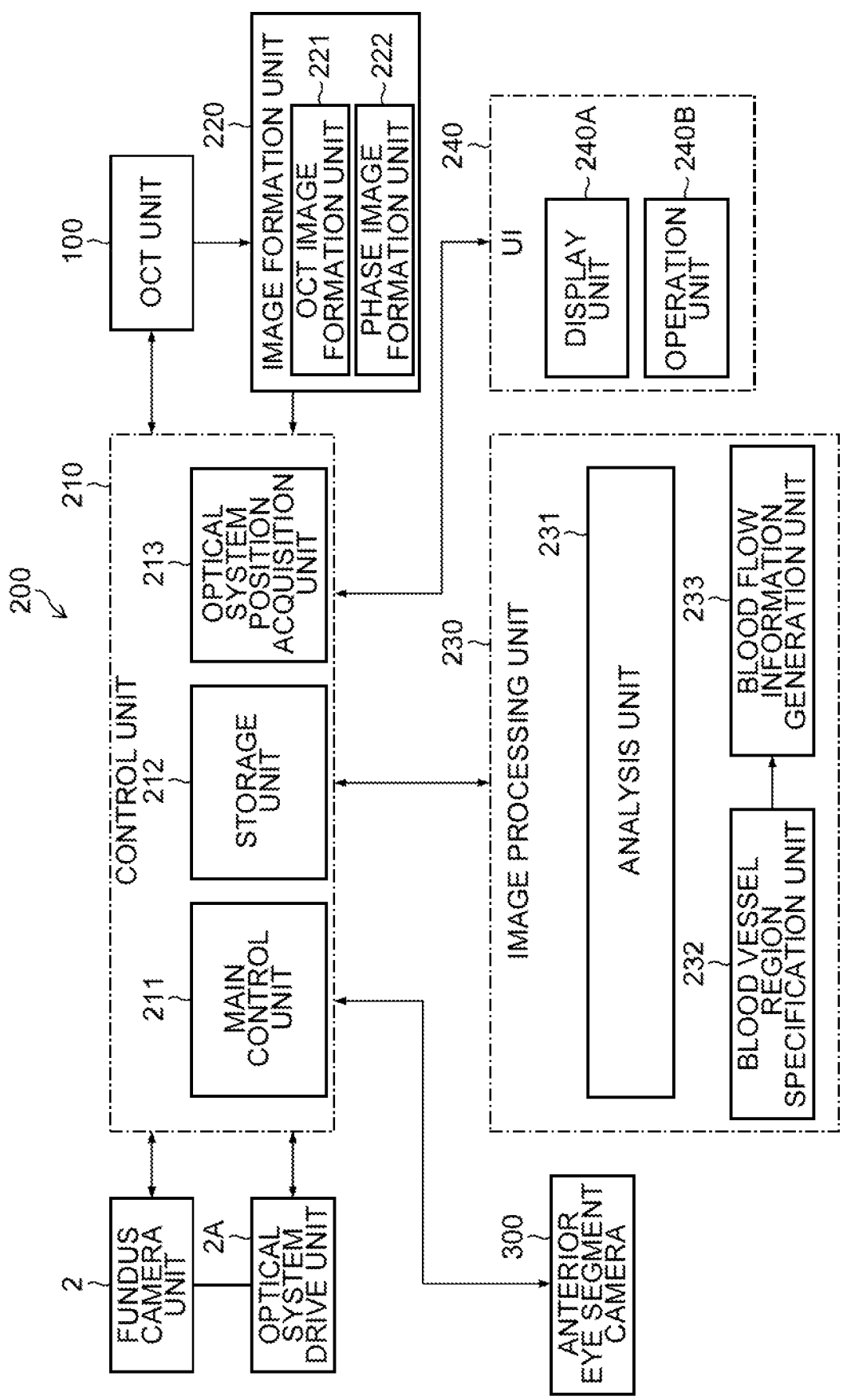
FIG. 4 is a block diagram illustrating a configuration of a computation control unit which is a control system of the ophthalmic device.

FIG. 4 is a block diagram illustrating a configuration of the computation control unit 200 which is a control system of the ophthalmic device 1.

(Control Unit)

As shown in FIG. 4, the computation control unit 200 is constructed centered on a control unit 210. The control unit 210 includes, for example, the aforementioned microprocessor, RAM, ROM, hard disk drive and communication interface. The control unit 210 is provided with a main control unit 211, a storage unit 212 and an optical system position acquisition unit 213.

(Main Control Unit)

The main control unit 211 performs the aforementioned various types of operation control. Note that the movement control of the focusing lens 31 is performed for controlling a focusing drive unit (not shown) to move the focusing lens 31 in the optical axis direction. The focusing position of the photographing optical system 30 is thereby changed. Furthermore, the main control unit 211 controls an optical system drive unit 2A to three-dimensionally move the examination optical system 1a (fundus camera unit 2 and the OCT unit 100) of the ophthalmic device 1 and also moves the aforementioned optical path length changing unit 41 in the direction indicated by the arrow shown in FIG. 1.

Since the anterior eye segment camera 300 of the present embodiment is provided in the fundus camera unit 2, the main control unit 211 can move the anterior eye segment camera 300 by controlling the optical system drive unit 2A. Note that a photographing movement unit can be provided which can move two or more anterior eye segment cameras 300 independently.

The main control unit 211 performs processing of writing data to the storage unit 212 and processing of reading data from the storage unit 212.

(Storage Unit)

The storage unit 212 stores various types of data. Examples of data stored in the storage unit 212 include image data of an OCT image, image data of a fundus image subject eye information and a position information table 219 (see FIG. 9) which will be described later. The subject eye information includes patient information relating to a subject such as the patient ID (identification) and the name, and information relating to the subject eye such as identification information of the left eye/right eye. Furthermore, the storage unit 212 stores various programs and data for operating the ophthalmic device 1. Though details will be described later, the position information table 219 is used for alignment of the examination optical system 1a during blood flow information measurement.

The storage unit 212 stores aberration information (not shown) in advance. The aberration information records information relating to distortion aberration produced in a photographed image due to the influence of the optical system mounted on each anterior eye segment camera 300. Here, the optical system mounted on the anterior eye segment camera 300 includes optical elements that produce, distortion aberration of, for example, lenses. The aberration information can be said to be a parameter that quantifies distortion given by the optical elements to the photographed image. Note that since a specific example of the method of generating aberration information is described, for example, in Japanese Patent Application Laid-Open No. 2013-248376 by the present applicant, detailed description thereof is omitted.

(Optical System Position Acquisition Unit)

The optical system position acquisition unit 213 acquires the current position of the examination optical system 1a mounted on the ophthalmic device 1. The examination optical system 1a is an optical system used to optically examine the subject eye E. The examination optical system 1a includes the photographing optical system 30 of the fundus camera unit 2 and the interference optical system 100a of the OCT unit 100, as has been already described.

The optical system position acquisition unit 213 receives an input of information indicating contents of movement control of the optical system drive unit 2A from, for example, the main control unit 211 and acquires the current position of the examination optical system 1a moved by the optical system drive unit 2A. A specific example of this processing will be described. The main control unit 211 controls the optical system drive unit 2A to move the examination optical system 1a to a predetermined initial position at predetermined timing (at the startup of the apparatus, when the patient information is inputted or the like). Thereinafter, the main control unit 211 records the control contents every time the optical system drive unit 2A is controlled. A history of the control contents is obtained in this way. The optical system position acquisition unit 213 acquires control contents up to the present with reference to this history and calculates the current position of the examination optical system 1a based on the control contents.

Furthermore, the main control unit 211 may also be configured to transmit (send) control contents to the optical system position acquisition unit 213 every time the main control unit 211 controls the optical system drive unit 2A, and the optical system position acquisition unit 213 may be configured to calculate the current position of the examination optical system every time the optical system position acquisition unit 213 receives the control contents. Alternatively, as another configuration example, the optical system position acquisition unit 213 may also be provided with a position sensor that detects the position of the examination optical system.

When the optical system position acquisition unit 213 acquires the current position of the examination optical system 1a as described above, the main control unit 211 can acquire positional deviation information of the examination optical system 1a with respect to the subject eye E based on the acquired current position and the three-dimensional position of the subject eye E obtained by an analysis unit 231 which will be described later. More specifically, the main control unit 211 recognizes the current position of the examination optical system 1a according to the result acquired by the optical system position acquisition unit 213 and recognizes the three-dimensional position of the subject eye E according to the analysis result obtained by the analysis unit 231.

Next, the main control unit 211 acquires positional deviation information including respective positional deviation amounts and positional deviation directions in the x direction (left-right direction), y direction (up-down direction) and z direction (operation distance direction) from appropriate positions of the examination optical system 1a with respect to the subject eye E based on the current position of the examination optical system 1a and the three-dimensional position recognized by the analysis unit 231. In this case, the main control unit 211 functions as a positional deviation information acquisition unit of the present invention.

The main control unit 211 performs alignment (hereinafter abbreviated as "first alignment") of the examination optical system 1a with respect to a reference position (e.g., cornea center) of the subject eye E through automatic control or manual control according to the acquired positional deviation information (positional deviation amount and positional deviation direction in each direction). In this case, the main control unit 211 and the optical system drive unit 2A function as the first alignment unit of the present invention. The first alignment includes alignment in a direction x, y direction) perpendicular to the optical axis direction (z direction) of the examination optical system 1a and alignment in the optical axis direction. Note that the optical axis direction (z direction) of the examination optical system 1a is an emission direction of light (signal light LS or the like) emitted from the objective lens 22 to the subject eye E and is the direction of the examination optical axis (photographing optical axis).

When performing automatic control, the main control unit 211 controls the optical system drive unit 2A so that the position of the examination optical system 1a with respect to the three-dimensional position of the subject eye E has a predetermined positional relationship, and changes the position thereof using the current position of the examination optical system 1a as the starting point. The predetermined positional relationship is such a relationship in which the positions in the x direction and the y direction coincide with each other and the distance in the z direction becomes a predetermined operation distance.

On the other hand, when performing manual control, the main control unit 211 displays an alignment index image superimposed on an observation image at a predetermined position on a screen of the display unit 240A according to the acquired positional deviation information (positional deviation amount and positional deviation direction at each direction). The display position and the size or the like of this alignment index image change according to the positional deviation amount and the positional deviation direction in each direction of the examination optical system 1a with respect to the subject eye E. The user (examiner) operates the operation unit 240B while checking the alignment index image displayed on the screen of the display unit 240A. Upon receiving this operation input, the main control unit 211 drives the optical system drive unit 2A to three-dimensionally move the examination optical system 1a and thereby performs first alignment.

(Image Formation Unit)

The image formation unit 220 forms image data of an OCT image (tomographic image) of the eye fundus Ef and image data of a phase image based on the detection signal from the image sensor 115. These images will be described later. The image format on unit 220 includes, for example, the aforementioned circuit substrate or a microprocessor. Note that the present specification may identify (treat as the same thing) "image data" with an "image" based on the image data. The image formation unit 220 includes an OCT image formation unit 221 and a phase image formation unit 222.

(OCT Image Formation Unit)

The OCT image formation unit 221 forms an OCT image (first OCT image) expressing a time-series variation in the form (shape) of the first cross section C0 based on the detection result of the interference light LC obtained through a first scan. The OCT image formation unit 221 also forms an OCT image (second OCT image) expressing the form (shape) of the second cross section C1 and an OCT image (second OCT image) expressing the form of the second cross section C2 based on the detection result of the interference light LC obtained by a second scan on the second cross sections C1 and C2. Since specific examples of the method of forming each OCT image are described in Japanese Patent Application Laid-Open No. 2013-208158 (PTL 2) by the present applicants, detailed description thereof is omitted.

Note that as with conventional spectral domain type optical coherence tomography, the processing of forming each OCT image includes processing of noise cancellation (noise reduction), filter processing and FFT (fast Fourier transform) or the like. In the case of another type OCT apparatus, the OCT image formation unit 221 executes well-known processing in accordance with the type.

(Phase Image Formation Unit)

The phase image formation unit 222 forms a phase image expressing a time-series variation of the phase difference on the first cross section, based on the interference light LC detection result obtained through the first scan. The detection result of the interference light LC used for this formation processing is the same as that used for the formation processing of the first OCT image by the OCT image formation unit 221. Therefore, it is possible to realize alignment between the first OCT image and the phase image. That is, it is possible to associate pixels of the first OCT image with pixels of the phase image. Note that since specific examples of the method of forming a phase image are described, for example, in Japanese Patent Application Laid-Open No. 2013-208158 (PTL 2) by the present applicants, detailed description thereof is omitted.

(Image Processing Unit)

The image processing unit 230 applies various types of image processing or analysis processing to an image (OCT image or the like) formed by the image formation unit 220. For example, the image processing unit 230 executes various types of correction processing such as brightness correction and scattering correction of images. Furthermore, the image processing unit 230 applies various types of image processing and analysis processing to images (fundus image, anterior eye segment image or the like) obtained by the fundus camera unit 2.

The image processing unit 230 executes well-known image processing such as interpolation processing of interpolating pixels between OCT images during OCT measurement and forms image data of the three-dimensional image of the eye fundus Ef. Note that image data of a three-dimensional image means image data in which pixel positions are defined by a three-dimensional coordinate system. Examples of image data of the three-dimensional image include image data made up of three-dimensionally arrayed voxels. This image data is called "volume data" or "voxel data" or the like. When an image based on volume data is displayed, the image processing unit 230 applies rendering processing to the volume data and thereby forms image data of a pseudo-three-dimensional image when seen from a specific sight line direction. This pseudo-three-dimensional image is displayed on the display device such as the display unit 240A.

Stack data of a plurality of OCT images can also be formed as image data of the three-dimensional image. The stack data is image data obtained by three-dimensionally arraying the plurality of OCT images obtained along a plurality of scan lines based on a positional relationship between scanning lines.

The image processing unit 230 includes the analysis unit 231 which correspond to a subject eye position acquisition unit of the present invention, a blood vessel region specification unit 232 and a blood flow information generation unit 233.

(Analysis Unit)

The analysis unit 231 analyzes two photographed images obtained by the anterior eye segment cameras 300A and 300B substantially simultaneously, and thereby obtains the three-dimensional position of the subject eye E. For example, the analysis unit 231 performs: correction processing of correcting distortion in each photographed image obtained by the anterior eye segment camera 300 based on aberration information stored in the storage unit 212; feature point specification processing of analyzing each photographed image and specifying a predetermined feature point (e.g., pupil center) of the anterior eye segment Ea; and three-dimensional position calculation processing of calculating the three-dimensional position of the subject eye E based on the position of the anterior eye segment camera 300 and the position of the feature point specified by the feature point specification processing. Note that since specific examples of the method of analyzing the three-dimensional position of the subject eye E are described, for example, in Japanese Patent Application Laid-Open No. 2013-248376 (PTL 1) by the present applicant, detailed description thereof is omitted.

(Blood Vessel Region Specification Unit)

The blood vessel region specification unit 232 specifies a blood vessel region corresponding to the concerned blood vessel Db for the first OCT image, the second OCT image and the phase image respectively during blood flow information measurement. This processing can be performed by analyzing pixel values of each image (e.g., threshold processing).

(Blood Flow Information Generation Unit)

The blood flow information generation unit 233 generates blood flow information relating to the concerned blood vessel Db based on the distance between the first cross section and the second cross section, the blood vessel region specification result and a time series variation in the phase difference in the blood vessel region of the phase image. Here, the distance between the first cross section and the second cross section (distance between cross sections) is determined in advance. The blood vessel region is obtained by the blood vessel region specification unit 232. The time-series variation of the phase difference in the blood vessel region of the phase image is obtained as a time-series variation of the phase difference about pixels in the blood vessel region of the phase image.

The blood flow information (blood flow velocity and blood flow rate or the like) is generated using a Doppler OCT technique. Since specific examples of the method of generating the blood flow information are described, for example, in Japanese Patent Application Laid-Open No. 2013-208158 (PTL 2) by the present applicants, detailed description thereof is omitted.

The blood flow velocity is calculated from the following [Expression 1], where the Doppler shift received by scattered light of the signal light LS is "Δf," the refractive index of blood is "n," the blood flow velocity is "v," the angle formed by the radiation direction of the signal light LS and the blood flow vector is "θ," and the central wavelength of the signal light LS is "λ." Note that n and λ are known, Δf is obtained from a time-series variation of the phase difference, and θ is obtained from a positional relationship between the blood vessel region of the first OCT image and the blood vessel regions of the two second OCT images.

$$\Delta f = \frac{2nv\cos\theta}{\lambda} \qquad \text{[Expression 1]}$$

The blood flow rate is calculated from the following [Expression 2], where the blood vessel diameter is "w," a maximum value of blood flow velocity is "Vm," and the blood flow rate is "Q."

$$Q = \frac{\pi w^2}{8} Vm \qquad \text{[Expression 2]}$$

The image processing unit 230 that functions as described above includes, for example, the aforementioned microprocessor, RAM, ROM, hard disk drive, circuit substrate and the like. The storage apparatus such as a hard disk drive stores in advance, a computer program that causes the microprocessor to execute the above-described functions.

(User Interface)

The user interface 240 marked "UI" in the drawing includes a display unit 240A and an operation unit 240B. The display unit 240A is provided with the display device and the display device 3 of the aforementioned computation control unit 200. The operation unit 240B is provided with the operation device of the aforementioned computation control unit 200. The operation unit 240B may also include a casing of the ophthalmic device 1 or various buttons and keys or the like provided outside the ophthalmic device 1. For example, when the fundus camera unit 2 includes a casing similar to that of a conventional fundus camera, the operation unit 240B may include a joystick and an operation panel or the like provided on the casing. The display unit 240A may include various display devices such as a touch panel provided on the casing of the fundus camera unit 2.

Note that the display unit 240A and the operation unit 240B need not be configured as individual devices. For example, a device such as a touch panel in which a display function and an operation function are integrated can also be used. In that case, the operation unit 240B is provided with a touch panel and a computer program. Contents of operation on the operation unit 240B are inputted to the control unit 210 as an electric signal. Operation and information input may also be performed using a graphical user interface (GUI) displayed on the display unit 240A and the operation unit 240B.

<Appearance of Ophthalmic Device>

Figure 5B:
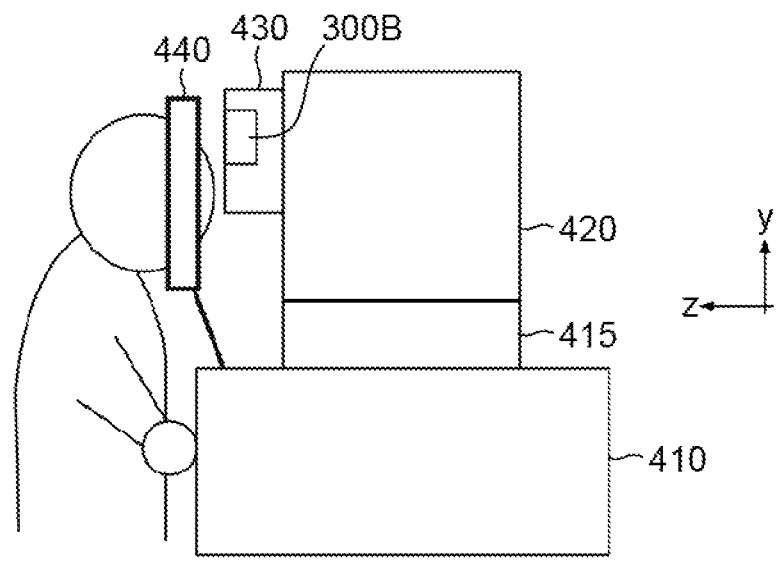
FIG. 5B is a side view of the ophthalmic device.

FIG. 5A is a front view of the ophthalmic device 1 and FIG. 5B is a side view of the ophthalmic device 1. As shown in FIG. 5A and FIG. 5B, the ophthalmic device 1 is provided with a jaw receiver and a forehead rest to support the subject's face. The jaw receiver and the forehead rest correspond to a support unit 440 in FIG. 5A and FIG. 5B. Reference numeral 410 designates a drive system of the optical system drive unit 2A or the like and a base in which the computation control circuit is accommodated. Reference numeral 415 designates a frame movably supported to the base 410. Reference numeral 420 designates a casing in which optical systems such as the fundus camera unit 2 and the OCT unit 100 and the photographing unit are accommodated. The casing 420 is provided on the frame 415. Reference numeral 430 designates a lens housing unit that projects in front of the casing 420 that houses the objective lens 22.

The aforementioned optical system drive unit 2A causes the frame 415 to move in the left-right direction (x direction), the up-down direction (y direction), and the front-back direction (z direction) to move the fundus camera unit 2 and the OCT unit 100 or the like accommodated in the casing 420 in the respective directions. That is, the optical system drive unit 2A causes the frame 415 to move in the xyz respective directions to thereby cause the examination optical system 1a together with the casing 420 to move in the xyz respective directions. Therefore, the aforementioned optical system position acquisition unit 213 may acquire, for example, the current position of the frame 415 as the current position of the examination optical system 1a.

<Movement of Frame during Blood Flow Information Measurement>

As described above, the blood flow information (blood flow velocity and blood flow rate) is generated using the technique of Doppler OCT. For this reason, when the examination optical system 1a is subjected to the first alignment, that is, when an angle θ (see the above [Expression 1]) formed by the incident direction of the signal light LS and the blood flow vector is 90°, the value of "cos θ" in [Expression 1] becomes 0, and so it is not possible to calculate the blood flow velocity. As a result, the blood flow rate expressed by the above [Expression 2] cannot be calculated either. Thus, in the blood flow information measurement, measurement is performed with the position of the examination optical system 1a shifted as shown in FIG. 6.

Figure 6:
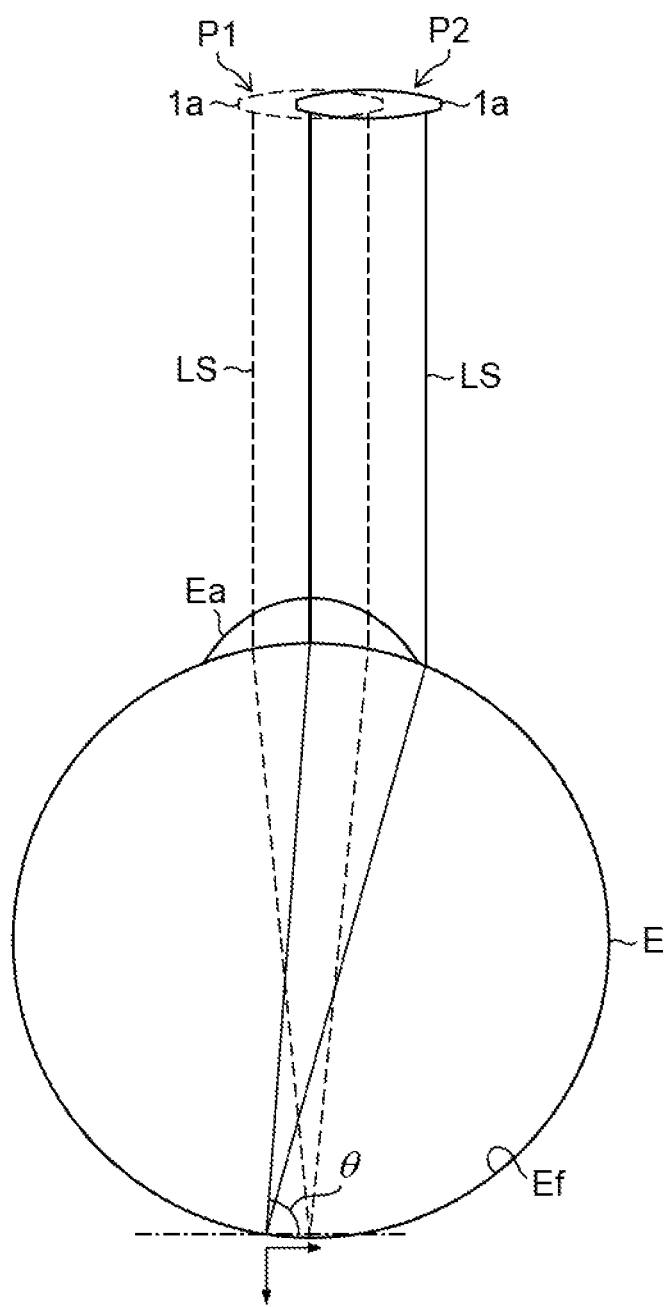
FIG. 6 is a schematic diagram illustrating a simplified view of a positional relationship between the subject eye and the examination optical system when measuring blood flow information.

FIG. 6 is a schematic diagram showing a simplified view of the positional relationship between the subject eye E and the examination optical system 1a during blood flow information measurement. As shown in FIG. 6, in the blood flow information measurement, the optical system drive unit 2A moves the frame 415 so that the examination optical system 1a is moved from a first position P1 at which the examination optical system 1a is subjected to first alignment to a second position P2 deviated in a direction perpendicular to the optical axis direction (z direction) of the examination optical system 1a. Thus, the signal light LS is made diagonally incident upon the eye fundus Ef from the second position P2, which causes the angle θ formed by the incident direction of the signal light LS and the blood flow vector to becomes less than 90°, making it possible to obtain blood flow information of the concerned blood vessel Db.

Note that the second position P2 is not particularly limited as long as the second position P2 is a position deviated from the first position P1 in a direction perpendicular to the z direction, and can be a position deviated from the first position P1 in any direction of the x direction, the y direction and the xy direction.

<Second Alignment During Blood Flow Information Measurement>

Thus, when the examination optical system 1a is moved from the first position P1 to the second position P2, a deviation is generated between the optical axis OA (see FIG. 7 or the like) of the examination optical system 1a and the reference position of the subject eye E [cornea center (Cornea vertex) in the present embodiment], and flare is thereby produced.

Figure 7:
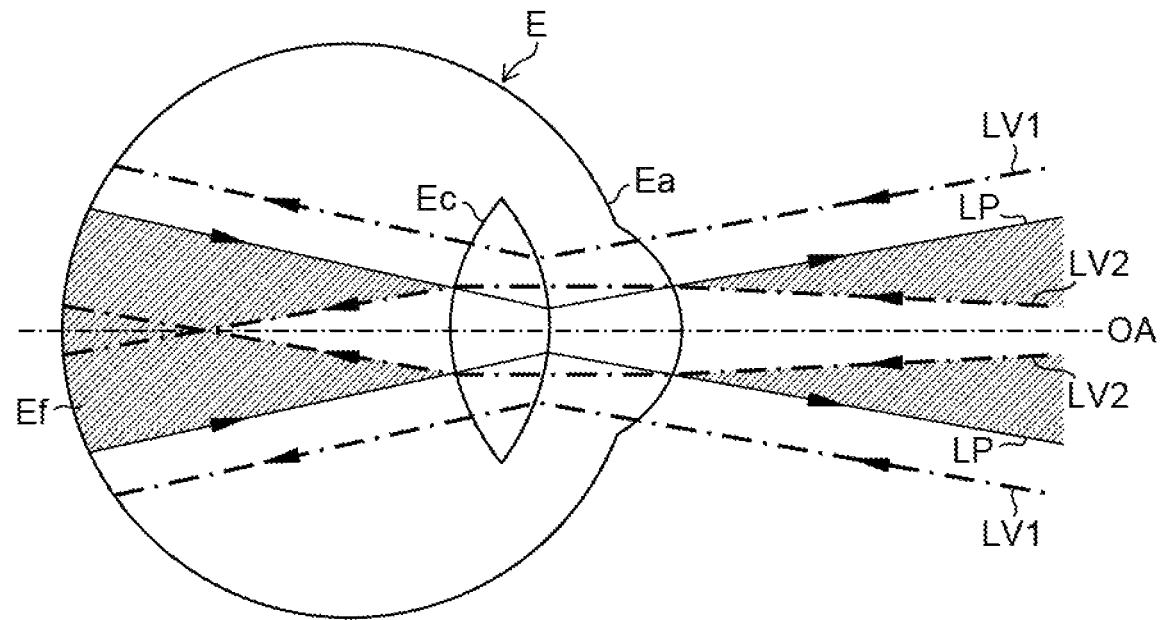
FIG. 7 is a schematic diagram illustrating an illumination luminous flux area (area of luminous flux for illumination) and a photographing luminous flux area of the ophthalmic device when the examination optical system is at a first position.
Figure 8:
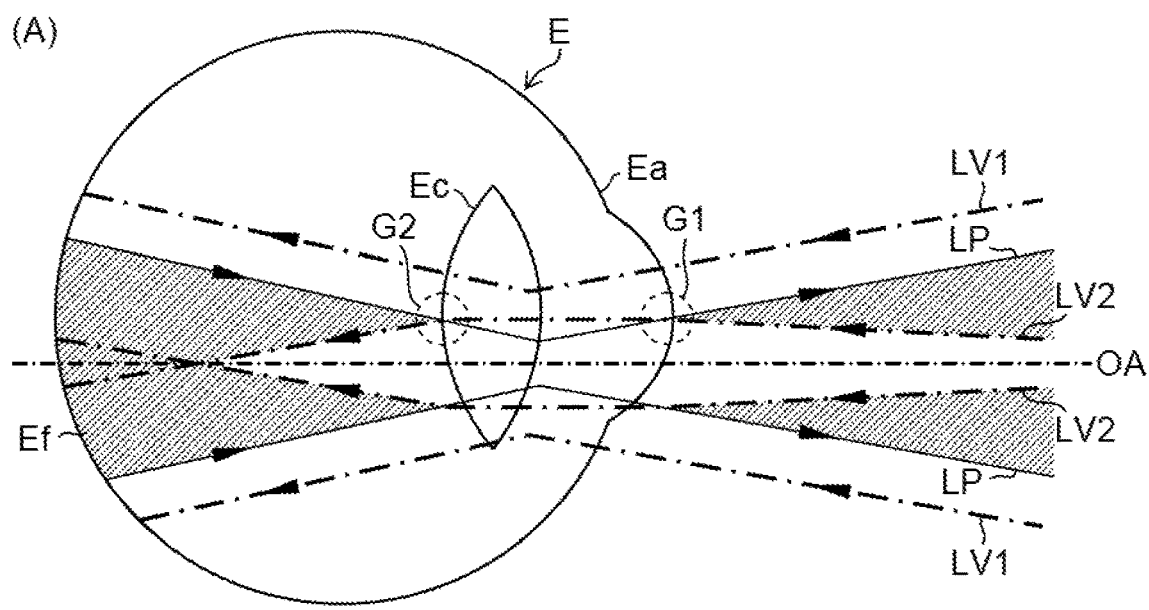
FIG. 8 shows Part (A) which is a schematic diagram illustrating an illumination luminous flux area and an photographing luminous flux area of the ophthalmic device when the examination optical system moves from the first position to the second position, Part (B) which is an enlarged view of a region designated by reference numeral G1 in Part (A), and Part (C) which is an enlarged view of a region designated by reference numeral G2 in Part (A).
Figure 8:
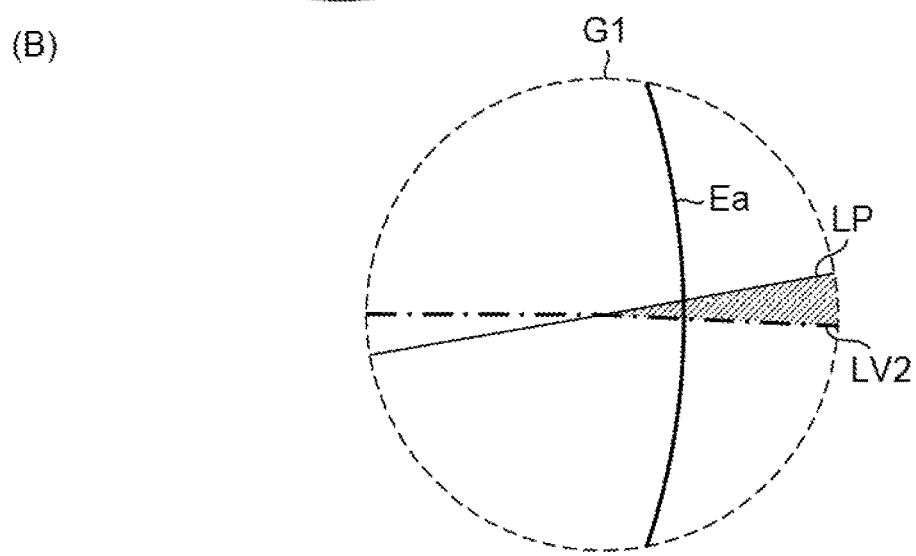
Figure 8:
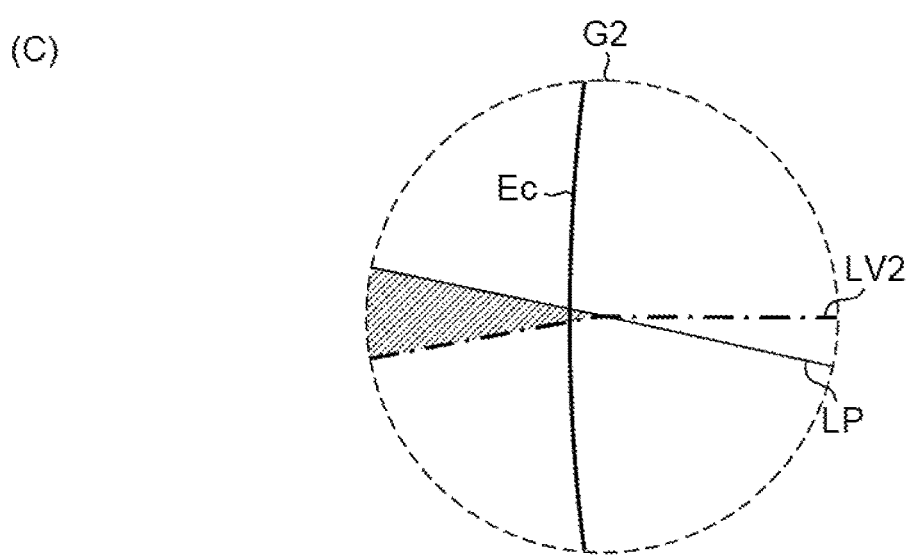

FIG. 7 is a schematic diagram illustrating an illumination luminous flux area (area of the illumination luminous flux) and a photographing luminous flux area (area of the photographing luminous flux) of the ophthalmic device 1 when the examination optical system 1a is located at the first position P1. Part (A) in FIG. 8 is a schematic diagram illustrating the illumination luminous flux area and the photographing luminous flux area of the ophthalmic device 1 when the examination optical system 1a moves from the first position P1 to the second position P2. Part (B) in FIG. 8 is an enlarged view of the region designated by reference numeral G1 in Part (A) in FIG. 8, and Part (C) is an enlarged view of the region designated by reference numeral G2 in Part (A) in FIG. 8.

In FIG. 7 and Part (A) to Part (C) in FIG. 8, the illumination luminous flux area in the vicinity of the pupil of the subject eye E formed by the aforementioned illumination optical system 10 and the photographing optical system 30 is located between an illumination luminous flux LV1 and an illumination luminous flux LV2 shown by single-dot dashed lines in the drawings. The photographing luminous flux area is formed by a photographing luminous flux LP shown by solid lines in the drawings.

As shown in FIG. 7, when the examination optical system 1a is located at the first position P1, that is, when the examination optical system 1a is subjected to the first alignment, the optical axis OA of the examination optical system 1a coincides with the position of the cornea center of the subject eye E and the operation distance (distance in the z direction) of the examination optical system 1a with respect to the subject eye E becomes an appropriate distance. In this case, an overlapping area where the illumination luminous flux area and the photographing luminous flux area overlap each other (shown by hatched area in the drawing), does not include (does not overlap with) neither the cornea of the anterior eye segment Ea nor the rear surface of the crystalline lens Ec.

On the other hand, as shown in Part (A) to Part (C) in FIG. 8, when the examination optical system 1a moves from the first position P1 to the second position P2, the optical axis OA of the examination optical system 1a remains deviated from the cornea center of the subject eye E while keeping the aforementioned operation distance. In this case, the overlapping area where the illumination luminous flux area and the photographing luminous flux area overlap each other, includes a part of the cornea of the anterior eye segment Ea and a part of the rear surface of the crystalline lens Ec. Due to this, flare is likely to occur.

Thus, when the examination optical system 1a is moved from the first position P1 to the second position P2, alignment of the examination optical system 1a in the z direction with respect to the subject eye E (hereinafter referred to as "second alignment") is automatically performed in the present embodiment.

(Functions of Main Control Unit)

Figure 9:
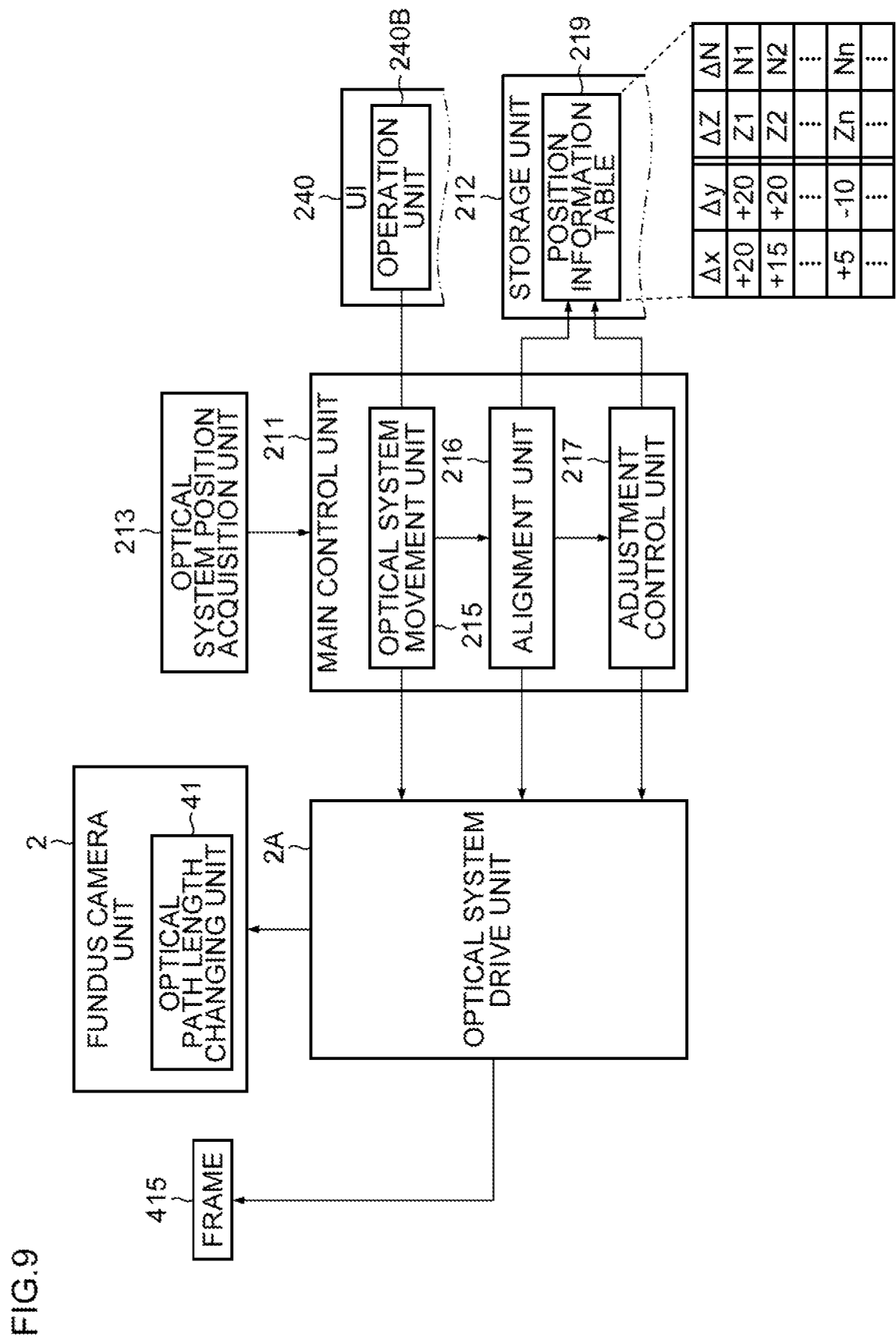
FIG. 9 is a functional block diagram illustrating functions of a main control unit after first alignment.

FIG. 9 is a functional block diagram illustrating functions of the main control unit 211 after the first alignment. As shown in FIG. 9 when the first alignment of the examination optical system 1a is completed in blood flow information measurement, the main control unit 211 functions as an optical system movement unit 215, an alignment unit 216 and an adjustment control unit 217.

The optical system movement unit 215 drives the optical system drive unit 2A to move the frame 415 in a direction perpendicular to the z direction according to the movement operation of the frame 415 performed by the user through the operation unit 240B after completion of the first alignment. In this way, the examination optical system 1a in the casing 420 is moved from the first position P1 to the second position P2. That is, the optical system movement unit 215 and the optical system drive unit 2A function as the optical system movement unit of the present invention.

Note that although the user manually moves the examination optical system 1a (frame 415) from the first position P1 to the second position P2 in the present embodiment, the optical system movement unit 215 may drive, for example, the optical system drive unit 2A to automatically move the examination optical system 1a to the second position P2 after completion of the first alignment.

The alignment unit 216 and the optical system drive unit 2A function as a second alignment unit of the present invention. The alignment unit 216 controls second alignment of the examination optical system 1a. When the optical system movement unit 215 causes the examination optical system 1a to move to the second position P2, the alignment unit 216 first acquires a positional difference in the x, y directions (hereinafter referred to as "xy positional difference") between the first position P1 and the second position P2.

The xy positional difference includes $\Delta x$ which is a difference in x coordinate and $\Delta y$ which is a difference in y coordinate between the first position P1 and second position P2. This xy positional difference can be acquired from the position of the examination optical system 1a acquired by, for example, the aforementioned optical system position acquisition unit 213. Note that the xy positional difference may also be acquired from a position detection sensor that can detect the position of the frame 415 (examination optical system 1a) such as an encoder provided in the optical system drive unit 2A or the frame 415.

Next, the alignment unit 216 determines an alignment position of the examination optical system 1a in the z direction (optical axis direction) with respect to the subject eye E at the second position P2 with reference to the position information table 219 stored in the storage unit 212 based on the acquired positional difference.

The position information table 219 stores a correspondence relation between the xy positional difference ($\Delta x$, $\Delta y$) and alignment position information $\Delta Z$ indicating the alignment position in the z direction. The alignment position information $\Delta Z$ is a positional difference between the z coordinate of the examination optical system 1a at the first position. P1 and the z coordinate of the examination optical system 1a aligned in the z direction at the second position P2. The alignment position information $\Delta Z$ is calculated through actual measurement or a simulation in advance for each combination pattern of the xy positional difference ($\Delta x$, $\Delta y$).

Thus, the alignment unit 216 can determine the alignment position in the z direction of the examination optical system 1a at the second position P2 corresponding to the xy positional difference ($\Delta x$, $\Delta y$) with reference to the position information table 219. The alignment unit 216 then performs the second alignment of the examination optical system 1a by controlling the optical system drive unit 2A based on the determined alignment position. In this way, the examination optical system 1a is moved to the alignment position along the z direction (optical axis direction).

Figure 10:
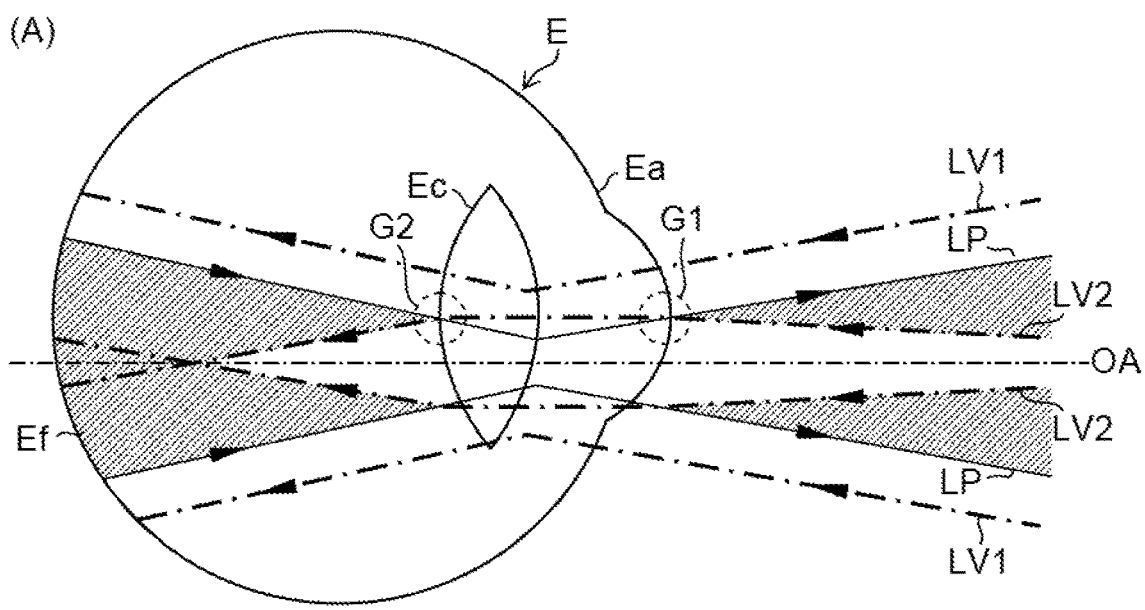
FIG. 10 shows Part (A) which is a schematic diagram illustrating the illumination luminous flux area and the photographing luminous flux area of the ophthalmic device when the second alignment is completed, Part (B) which is an enlarged view of a region designated by reference numeral G1 in Part (A), and Part (C) which is an enlarged view of a region designated by reference numeral G2 in Part (A).
Figure 10:
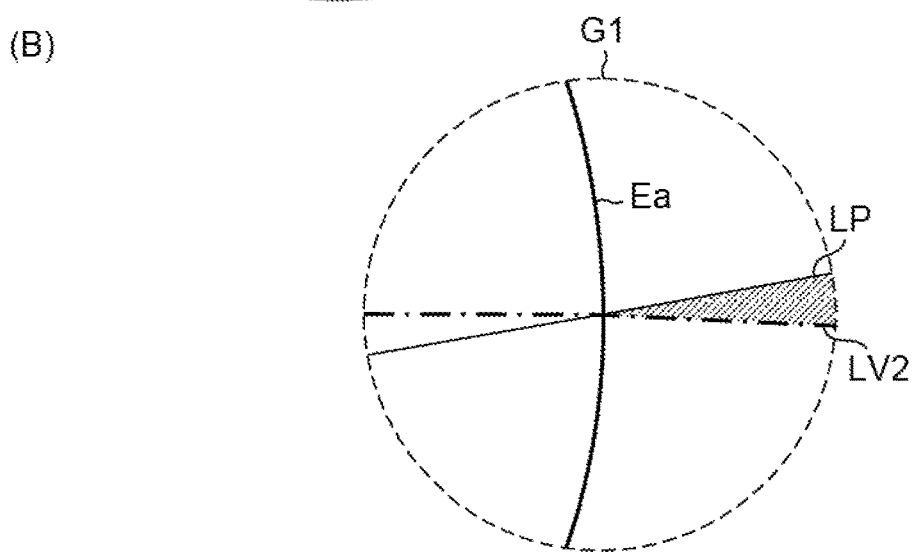
Figure 10:
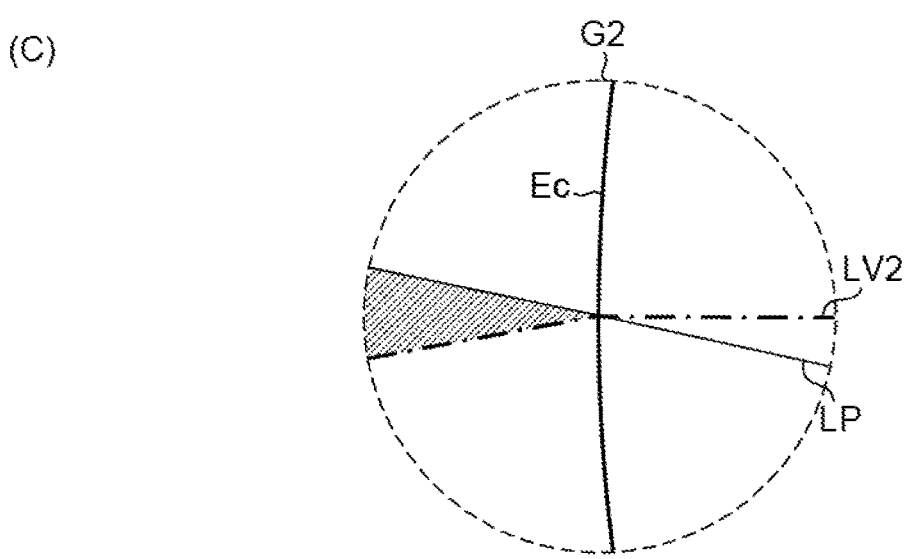

Part (A) in FIG. 10 is a schematic diagram illustrating an illumination luminous flux area and an photographing luminous flux area of the ophthalmic device 1 after completion of the second alignment. Part (B) in FIG. 10 is an enlarged view of the region designated by reference numeral G1 in Part (A) in FIG. 10. Part (C) in FIG. 10 is an enlarged view of the region designated by reference numeral G2 in Part (A) in FIG. 10.

As shown in Part (A) to Part (C) in FIG. 10, when the examination optical system 1a is subjected to the second alignment, the overlapping area where the illumination luminous flux area and the photographing luminous flux area overlap each other (portions shown by hatched area in the drawing) does not include (doses not overlap with) neither the cornea of the anterior eye segment Ea nor the rear surface of the crystalline lens Ec. Alternatively, the overlapping area includes smaller part of the cornea of the anterior eye segment Ea and smaller part of the rear surface of the crystalline lens Ec, compared to the state before the second alignment shown in Part (A) to Part (C) in FIG. 8 described above.

Returning to FIG. 9, the position information table 219 stores movement information $\Delta N$ indicating the direction and the distance the aforementioned optical path length changing unit 41 is moved according to the second alignment of the examination optical system 1a in association with each xy positional difference ($\Delta x$, $\Delta y$) [alignment position information $\Delta Z$].

When the examination optical system 1a is subjected to the second alignment, the optical path length of the signal light LS changes, and so the optical path length difference between the signal light LS and the reference light LR changes from the state before the second alignment. Therefore, in the present embodiment, movement information $\Delta N$ of the optical path length changing unit 41 that can keep the optical path length difference constant (unchanged) even when the examination optical system 1a is subjected to the second alignment, is obtained in advance for each combination pattern of xy positional difference ($\Delta x$, $\Delta y$) through measurement or a simulation or the like, and the movement information $\Delta N$ is stored in the position information table 219. In this way, the movement information $\Delta N$ of the optical path length changing unit 41 corresponding to the xy positional difference ($\Delta x$, $\Delta y$) can be obtained with reference to the position information table 219.

The adjustment control unit 217 controls the optical system drive unit 2A according to the second alignment of the examination optical system 1a to move the optical path length changing unit 41, and thereby adjusts the optical path length of the signal light LS.

To be more specific, when the examination optical system 1a is subjected to the second alignment, the adjustment control unit 217 acquires the xy positional difference (Δx, Δy) or the alignment position information ΔZ from the alignment unit 216. Next, the adjustment control unit 217 acquires the movement information ΔN corresponding to the xy positional difference (Δx, Δy) with reference to the position information table 219 based on the acquired xy positional difference (Δx, Δy). The adjustment control unit 217 controls the optical system drive unit 2A based on the acquired movement information ΔN to cause the optical path length changing unit 41 to move. In this way, in accordance with the distance and the direction that the examination optical system 1a moves in the z direction in the second alignment, the optical path length of the signal light LS is adjusted so that the optical path length difference is kept constant.

Note that as described above, the optical path length of the reference light LR may be adjusted or optical path lengths of both the signal light LS and the reference light LR may be adjusted, instead of adjusting the optical path of the signal light LS.

<Operation of Ophthalmic Device>

Figure 11:
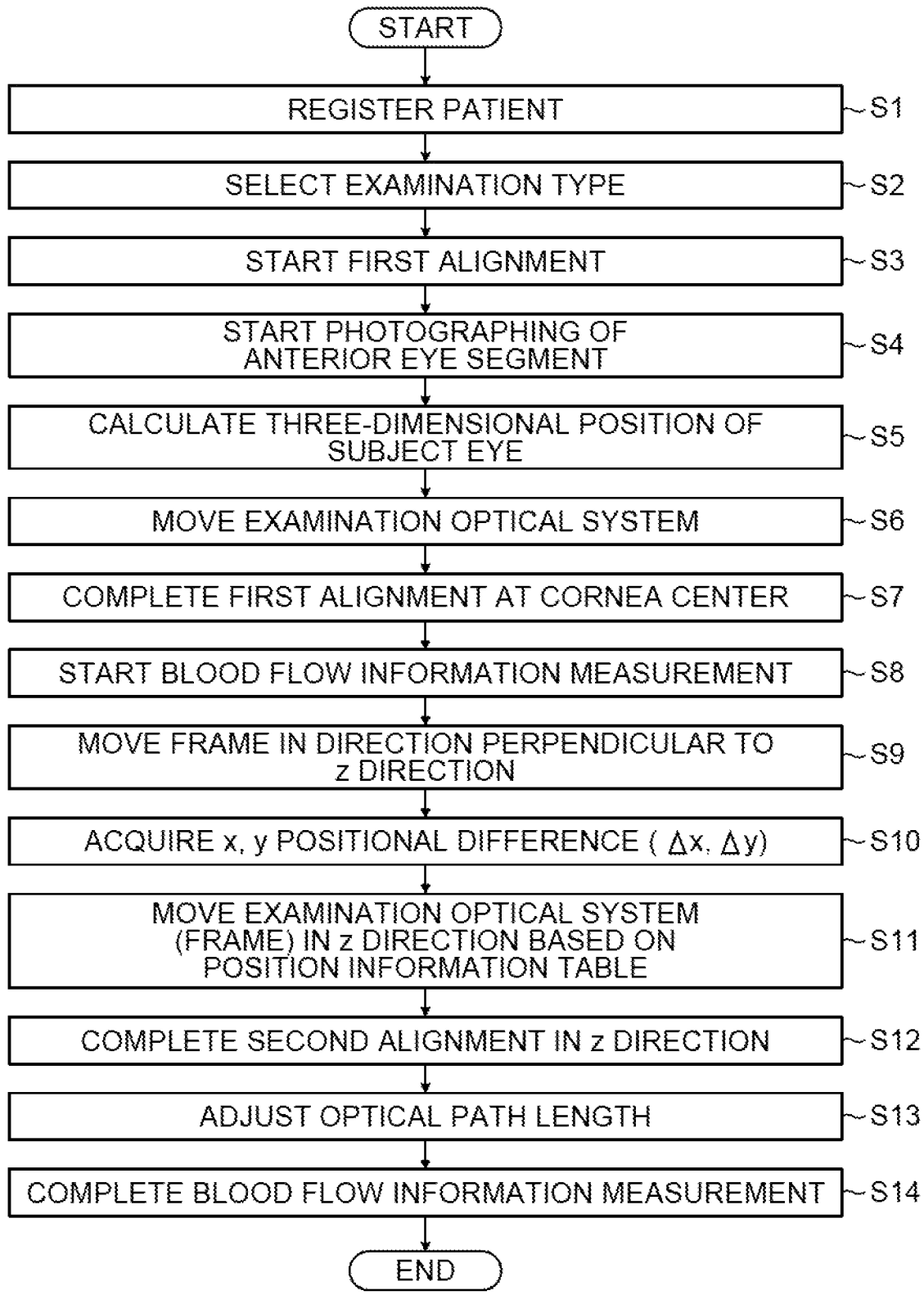
FIG. 11 is a flowchart illustrating a flow of measurement processing of blood flow information of the eye fundus in the ophthalmic device.

Next, measurement processing of blood flow information of the eye fundus Ef by the ophthalmic device 1 in the above-described configuration will be described using FIG. 11. FIG. 11 is a flowchart illustrating a flow of measurement processing of the blood flow information of the eye fundus Ef by the ophthalmic device 1.

The user turns ON power of the ophthalmic device 1 and then enters patient information including the patient ID and the patient name of a subject using the user interface 240 (step S1). The patient information is stored in the storage unit 212.

Next, the user selectively enters the type of an examination to be carried out on the subject using the user interface 240. Examples of items of the examination type include an examination region (fundus central part, fundus periphery, optic papilla, macula or the like), subject eye (left eye, right eye, both eyes), photographing pattern (fundus image only, OCT image only, both of them), OCT scan pattern (line scan, cross scan, radial scan, circular scan, three-dimensional scan or the like), and measurement item (blood flow information or the like). Measurement of the blood flow information of the eye fundus Ef is selected in the present embodiment (step S2).

(First Alignment)

When the selection of the examination type is completed and after the subject's face is supported to the support unit 440, the user instructs starting of first alignment using the user interface 240 (step S3). Note that the starting of the first alignment may be automatically instructed after the selection of the examination type.

Upon receiving the instruction of starting of the first alignment, the main control unit 211 causes the anterior eye segment cameras 300A and 300B to start photographing (moving image photographing) of the anterior eye segment Ea (step S4). Thus, photographed images (frames) of the anterior eye segment Ea respectively photographed by the anterior eye segment cameras 300A and 300B are inputted to the analysis unit 231 via the control unit 210.

The analysis unit 231 that has received the photographed images of the anterior eye segment Ea from the control unit 210 as input performs the aforementioned correction processing, feature point specification processing and three-dimensional position calculation processing to thereby calculate the three-dimensional position of the subject eye E and outputs the calculation result to the main control unit 11 (step S5). The optical system position acquisition unit 213 acquires the current position of the examination optical system 1a and outputs the acquired current position to the main control unit 211.

The main control unit 211 receives the calculation result of the three-dimensional position of the subject eye E and the current position of the examination optical system 1a as input, and then acquires positional deviation information of the examination optical system 1a with respect to the cornea center of the subject eye E (amount of positional deviation in each direction of xyz from an appropriate position and positional deviation direction).

When the main control unit 211 carries out the first alignment through automatic control, the main control unit 211 controls the optical system drive unit 2A to move the frame 415 (examination optical system 1a) so that the position of the examination optical system 1a with respect to the three-dimensional position of the subject eye E has a predetermined positional relationship based on the positional deviation information (step S6).

On the other hand, when the main control unit 211 carries out the first alignment through manual control, the main control unit 211 displays a composite image with the alignment index image superimposed on the observation image at a predetermined position on the screen of the display unit 240A based on the positional deviation information. Next, the user operates the operation unit 240B to move the frame 415 (examination optical system 1a) so that the position of the examination optical system 1a with respect to the three-dimensional position of the subject eye E has a predetermined positional relationship (step S6).

When the movement of the examination optical system 1a is completed, the first alignment of the examination optical system 1a with respect to the cornea center of the subject eye E is completed (step S7). A step of measuring the blood flow information of the eye fundus Ef is then started (step S8). In this case, the main control unit 211 functions as the optical system movement unit 215, the alignment unit 216 and the adjustment control unit 217 (see FIG. 9).

(Second Alignment)

Using the operation unit 240B, the user performs a movement operation to move the frame 415 in a direction perpendicular to the z direction. Upon receiving the movement operation, the optical system movement unit 215 controls the optical system drive unit 2A to move the frame 415 in the perpendicular direction (step S9). Thus, as shown in FIG. 6 described above, the examination optical system 1a in the casing 420 is moved from the first position P1 to the second position P2. Note that the movement of the frame 415, that is, the movement of the examination optical system 1a to the second position P2 may be automatically performed by the optical system movement unit 215 after completion of the first alignment.

When the movement of the examination optical system 1a to the second position P2 is performed, the alignment unit 216 acquires the positions of the examination optical system 1a before and after the movement to the second position P2, from the optical system position acquisition unit 213. In this way the alignment unit 216 acquires an xy positional difference (Δx, Δy) between the first position P1 and the second position P2 (step S10).

Next, as shown in FIG. 9 above, the alignment unit 216 determines the alignment position in the z direction of the examination optical system 1a with respect to the subject eye E at the second position P2 with reference to the position information table 219 in the storage unit 212 based on the acquired xy positional difference ($\Delta x$, $\Delta y$). The alignment unit 216 controls the optical system drive unit 2A based on the determined alignment position to move the frame 415 along the z axis direction (step S11). This causes the examination optical system 1a to move to the alignment position along the z axis direction (optical axis direction), thus completing the second alignment in the z direction of the examination optical system 1a with respect to the subject eye E (step S12).

By performing the second alignment of the examination optical system 1a in this way, the overlapping area where the illumination luminous flux area and the photographing luminous flux area overlap each other, can be set so as not to include the cornea of the anterior eye segment Ea and the rear surface of the crystalline lens Ec, or so as to include smaller part of them. Thus, it is possible to reduce generation of flare.

(Adjustment of Optical Path Length)

When the second alignment is performed, the adjustment control unit 217 acquires the movement information $\Delta N$ corresponding to the xy positional difference ($\Delta x$, $\Delta y$) or the like with reference to the position information table 219 based on the xy positional difference ($\Delta x$, $\Delta y$) or the like acquired from the alignment unit 216. The adjustment control unit 217 controls the optical system drive unit 2A based on the acquired movement information $\Delta N$ to move the optical path length changing unit 41. Thus, the optical path length of the signal light LS is adjusted so as to keep the optical path length difference between the signal light LS and the reference light LR constant before and after the second alignment (step S13). As a result, it is possible to prevent the depth of the eye fundus Ef at which the OCT image is obtained from changing before and after the second alignment.

(Blood Flow Information Measurement)

After completion of the second alignment and the adjustment of the optical path length, the user instructs the operation unit 240B to start blood flow information measurement. Note that an instruction to start blood flow information measurement may be given automatically after completion of the second alignment and an adjustment of the optical path length. Upon receiving the instruction to start blood flow information measurement, the ophthalmic device 1 performs the aforementioned first scan and second scan on the concerned blood vessel Db (see FIG. 3). Thus, the OCT image formation unit 221 forms a first OCT image and a second OCT image, and the phase image formation unit 222 forms a phase image. Next, the blood vessel region specification unit 232 specifies the blood vessel region corresponding to the concerned blood vessel Db, and then the blood flow information generation unit 233 generates blood flow information relating to the concerned blood vessel Db.

The measurement of the blood flow information relating to the concerned blood vessel Db is now complete (step S14). The measurement result of the blood flow information relating to the concerned blood vessel Db is stored in the storage unit 212 in association with the aforementioned patient information.

<Effects of Present Embodiment>

As described above, according to the ophthalmic device 1 of the present embodiment, it is possible to determine the alignment position in the z direction of the examination optical system 1a at the second position P2 by only referencing the position information table 219 based on the xy positional difference ($\Delta x$, $\Delta y$) between the first position P1 and the second position P2 when the examination optical system 1a is moved from the first position P1 to the second position P2. As a result, it is possible to determine the alignment position more simply and more quickly than in the prior arts.

FIG. 12 is a flowchart illustrating a flow of blood flow information measurement processing of the eye fundus Ef in a comparative example in which the method described in the above PTL 3 is adopted. As shown in FIG. 12, since processes from step S1 to step S9 are basically identical to those in the present embodiment, detailed description thereof is omitted here.

When the examination optical system 1a is moved from the first position P1 to the second position P2 along with the movement of the frame 415 in step S9, in the comparative example, photographed images of the anterior eye segment Ea of the subject eye E photographed by the anterior eye segment cameras 300A and 300B are analyzed and an amount of misalignment in the xy direction at the second position with respect to the first position P1 is detected (step S10A).

Next, in the comparative example, the alignment position in the z direction of the examination optical system 1a is calculated based on the detected amount of misalignment (step S10B). Subsequent processing is basically identical to that of the present embodiment, and so detailed description thereof is omitted.

In this way, it is necessary to detect the amount of misalignment through an image analysis and perform computation processing of the alignment position in the z direction after moving the examination optical system 1a to the second position P2 and before starting the second alignment in the comparative example, and so the second alignment takes more time. When a high performance computation processing apparatus is used to shorten the time, the manufacturing cost of the ophthalmic device 1 increases.

Compared to such a comparative example, the ophthalmic device 1 of the present embodiment directly detects the movement of the frame 415 (examination optical system 1a) and can thereby simply detect the xy positional difference ($\Delta x$, $\Delta y$) between the first position P1 and the second position P2 without performing the image analysis as shown in the comparative example. Furthermore, the ophthalmic device 1 of the present embodiment can simply determine the alignment position in the z direction by only referencing the position information table 219, which eliminates the necessity for the processing as shown in step S10B in the comparative example. As a result, the ophthalmic device 1 of the present embodiment can perform the second alignment at lower cost and in a shorter time without using a high performance computation processing apparatus.

<Modifications>

A position deviated in the direction perpendicular to the z direction from the first position P1 has been described in the above-described embodiment as an example of the second position P2 of the examination optical system 1a in blood flow information measurement (see FIG. 6). However, the second position P2 is not particularly limited, as long as the second position P2 is located at a position deviated at least in a direction perpendicular to the z direction from the first position P1. The second position P2 may be a position deviated in both the direction perpendicular to the z direction and the z direction. For example, the second position P2 may be located at a position deviated in any one of the xz direction, the yz direction and the xyz direction with respect to the first position P1.

Note that in this case, the position information table 219 shown in FIG. 9 described above stores the positional difference ($\Delta x$, $\Delta y$, $\Delta z$) in the x, y, z directions between the first position P1 and the second position P2, and a correspondence relation between the alignment position information ΔZ and movement information ΔN.

In the above-described embodiment, the position information table 219 is stored in the storage unit 212 as the information representing the correspondence relation between the positional difference between the first position P1 and the second position P2, and the alignment position in the z direction. However, a calculation expression representing the aforementioned correspondence relation may be stored in the storage unit 212 instead of the position information table 219.

In the above-described embodiment, the examination optical system 1a is moved relative to the subject eye E by moving the frame 415. However, the method of moving the examination optical system 1a relative to the subject eye E is not particularly limited, and other well-brown techniques may also be used.

In the above-described embodiment, images acquired by the anterior eye segment cameras 300A and 300B are analyzed by the analysis unit 231 to thereby acquire the three-dimensional position of the subject eye E. However, various well-known methods may also be used as the method of acquiring the three-dimensional position of the subject eye E.

Although the ophthalmic device 1 has been described in the above-described embodiment where the examination optical system 1a is moved from the first position. P1 to the second position P2 to measure blood flow information of the eye fundus Ef which is the region to be observed of the subject eye E, the present invention is also applicable to an ophthalmic device which performs various types of measurement of the region to be observed of the subject eye E at a position where the examination optical system 1a is moved in a direction perpendicular to at least the z direction from the first position P1. Examples of this ophthalmic device include not only an optical interference tomograph meter using OCT but also a scanning laser ophthalmoscope (SLO) which obtains an image of the eye fundus with laser scan using a confocal optical system, a slit lamp which acquires an image by cutting an optical slice of the cornea using slit light, an eye refraction examination apparatus (refractometer, keratometer) which measures refraction characteristics of the subject eye, an ophthalotonometer, a specular microscope which obtains characteristics (cornea thickness, cell distribution or the like) of the cornea and a wavefront analyzer which obtains aberration information of a subject eye using a Shack-Hartmann sensor.

REFERENCE SIGNS LIST 1 ophthalmic device, 1a examination optical system, 2 fundus camera unit, 2A optical system drive unit, 30 photographing optical system, 41 optical path length changing unit, 100 OCT unit, 100a interference optical system, 115 image sensor, 210 control unit, 211 main control unit, 212 storage unit, 213 optical system position acquisition unit, 215 optical system movement unit, 216 alignment unit, 217 adjustment control unit, 219 position information table, 220 image formation unit, 231 analysis unit, 232 blood vessel region specification unit, 233 blood flow information generation unit, 240 user interface, 240B operation unit, 300, 300A, 300B anterior eye segment camera 300, 415 frame, 420 casing

The invention claimed is:

1. An ophthalmic device comprising:
   a photographing unit configured to photograph a region to be observed of a subject eye through an examination optical system;
   a first alignment unit configured to perform alignment of the examination optical system respect to the subject eye in an optical axis direction and alignment in a perpendicular direction to the optical axis direction;
   an optical system movement unit configured to move the examination optical system from a first position aligned by the first alignment unit to a second position deviated at least in the perpendicular direction; and
   a second alignment unit configured to determine an alignment position in the optical axis direction of the examination optical system at the second position with respect to the subject eye based on a positional difference between the first position and the second position, and move the examination optical system to the alignment position along the optical axis direction.

2. The ophthalmic device according to claim 1, wherein the examination optical system further comprises:
   an interference optical system configured to divide light emitted from a light source into signal light and reference light, irradiate the region to be observed with the signal light and guide interference light between the signal light reflected by the region to be observed and the reference light to the photographing unit;
   an optical path length changing unit provided in the interference optical system and configured to change an optical path length of at least one of the signal light and the reference light; and
   an adjustment control unit configured to control the optical path length changing unit to adjust the optical path length according to a distance and a direction that the examination optical system moves in the optical axis direction in alignment by the second alignment unit.

3. The ophthalmic device according to claim 1, further comprising:
   a base; and
   a frame supported movably with respect to the base at least in the perpendicular direction, wherein
   the examination optical system and the photographing unit are disposed on the frame, and
   the optical system movement unit moves the frame to move the examination optical system from the first position to the second position.

4. The ophthalmic device according to claim 1, further comprising
   a storage unit configured to store a correspondence relation between the positional difference and the alignment position,
   wherein the second alignment unit refers to the correspondence relation stored in the storage unit based on the positional difference and determines the alignment position.

5. The ophthalmic device according to claim 1, further comprising:
   a subject eye position acquisition unit configured to acquire a three-dimensional position of the subject eye; and
   a positional deviation information acquisition unit configured to acquire positional deviation information of the examination optical system in the optical axis direction and the perpendicular direction with respect to the subject eye based on the three-dimensional position acquired by the subject eye position acquisition unit, wherein the first alignment unit performs alignment of the examination optical system through automatic control or manual control based on the positional deviation information acquired by the positional deviation information acquisition unit.

* * * * *